US009493355B2

(12) United States Patent
Tour et al.

(10) Patent No.: US 9,493,355 B2
(45) Date of Patent: Nov. 15, 2016

(54) SOLVENT-BASED METHODS FOR PRODUCTION OF GRAPHENE NANORIBBONS

(75) Inventors: James M. Tour, Bellaire, TX (US); Wei Lu, Houston, TX (US); Bostjan Genorio, Ivancna Gorica (SI)

(73) Assignee: WILLIAM MARSH RICE UNIVERSITY, Houston, TX (US)

( * ) Notice: Subject to any disclaimer, the term of this patent is extended or adjusted under 35 U.S.C. 154(b) by 219 days.

(21) Appl. No.: 14/345,016

(22) PCT Filed: Sep. 14, 2012

(86) PCT No.: PCT/US2012/055414
§ 371 (c)(1),
(2), (4) Date: Nov. 14, 2014

(87) PCT Pub. No.: WO2013/040356
PCT Pub. Date: Mar. 21, 2013

(65) Prior Publication Data
US 2015/0057417 A1 Feb. 26, 2015

Related U.S. Application Data

(60) Provisional application No. 61/534,553, filed on Sep. 14, 2011.

(51) Int. Cl.
*C01B 31/02* (2006.01)
*C07C 29/32* (2006.01)
*C08F 112/08* (2006.01)
*C01B 31/04* (2006.01)

(52) U.S. Cl.
CPC ....... *C01B 31/0293* (2013.01); *C01B 31/0273* (2013.01); *C01B 31/0286* (2013.01); *C01B 31/0446* (2013.01); *C01B 31/0484* (2013.01); *C07C 29/32* (2013.01); *C08F 112/08* (2013.01); *C01B 2204/06* (2013.01)

(58) Field of Classification Search
CPC ... C01B 31/0293; C07C 29/32; C08F 112/08
USPC .......... 524/495; 526/89; 568/840; 423/437.1
See application file for complete search history.

(56) References Cited

U.S. PATENT DOCUMENTS

| 2006/0239891 | A1* | 10/2006 | Niu ........................ | B82Y 30/00 423/445 R |
| 2008/0128688 | A1 | 6/2008 | Pan et al. | |
| 2009/0029221 | A1 | 1/2009 | Goddard et al. | |
| 2010/0028681 | A1 | 2/2010 | Dai et al. | |
| 2010/0055458 | A1* | 3/2010 | Jang ........................ | B82Y 30/00 428/402 |
| 2010/0096597 | A1 | 4/2010 | Prud'Homme et al. | |
| 2010/0105834 | A1 | 4/2010 | Tour et al. | |
| 2010/0140792 | A1* | 6/2010 | Haddon ................ | B82Y 30/00 257/713 |
| 2010/0233067 | A1* | 9/2010 | Fukuzumi .............. | B82Y 30/00 423/447.2 |
| 2011/0017587 | A1* | 1/2011 | Zhamu ................... | B82Y 30/00 204/157.62 |
| 2011/0017955 | A1 | 1/2011 | Zhamu et al. | |
| 2011/0068290 | A1* | 3/2011 | Haddon ............... | C12Q 1/6881 252/62.51 R |

FOREIGN PATENT DOCUMENTS

| WO | WO-2010147860 A1 | 12/2010 |
| WO | 20110014347 | 2/2011 |
| WO | 2013040356 | 3/2013 |

OTHER PUBLICATIONS

European Patent Office, Extended Search Report and Search Opinion dated Sep. 29, 2015 for Application No. EP12832239.3, "Solvent-Based Methods for Production of Graphene Nanoribbons", William Marsh Rice University, applicant.
Kosynkin et al. "Longitudnal unzipping of carbon nanotubes to form graphene nanoribbons." Nature Letters, Apr. 16, 2009, vol. 458, pp. 872-877.
Li, et al. "Oxygen-Driven Unzipping of Graphitic Materials." Physical Review Letters, May 5, 2006, vol. 96, pp. 1-4.
Sinitskii et al. "Kinetics of Diazonium Functionalization of Chemically Converted Graphene Nanoribbons." ACS Nano, Mar. 26, 2010, vol. 4, No. 4, pp. 1949-1954.
Sinitskii et al. "Electronic Transport in Monolayer Graphene Nanoribbons Produced by Chemical Unzipping of Carbon Nanotubes." Applied Physics Letters, Dec. 23, 2009, vol. 95, pp. 1-3.
Han et al. "Energy band-gap engineering of graphene nanoribbons." Phys. Rev. Lett. 98, 206805/1-206805/4 (2007).
Schniepp et al. "Functionalized Single Graphene Sheets Derived from Splitting Graphite Oxide." J. Phys. Chem. B 110, 8535-8539 (2006).
Chen et al. "Graphene nano-ribbon electronics." Physica E 40, 228-232 (2007).

(Continued)

*Primary Examiner* — Ling Choi
*Assistant Examiner* — Ronald Grinsted
(74) *Attorney, Agent, or Firm* — Winstead PC

(57) ABSTRACT

The present invention provides methods of preparing functionalized graphene nanoribbons. Such methods include: (1) exposing a plurality of carbon nanotubes (CNTs) to an alkali metal source in the presence of an aprotic solvent to open them; and (2) exposing the opened CNTs to an electrophile to form functionalized graphene nanoribbons (GNRs). The methods may also include a step of exposing the opened CNTs to a protic solvent to quench any reactive species on them. Additional methods include preparing unfunctionalized GNRs by: (1) exposing a plurality of CNTs to an alkali metal source in the presence of an aprotic solvent to open them; and (2) exposing the opened CNTs to a protic solvent to form unfunctionalized GNRs.

18 Claims, 39 Drawing Sheets

(56) References Cited

OTHER PUBLICATIONS

Rollings et al. "Synthesis and characterization of atomically thin graphite films on a silicon carbide substrate." J. Phys. Chem. Solids 67, 2172-2177 (2006).
Li et al. "Chemically Derived, Ultrasmooth Graphene Nanoribbon Semiconductors." Science 319, 1229-1232 (2008).
Campos-Delgado et al. "Bulk Production of a New Form of sp2 Carbon: Crystalline Graphene Nanoribbons." Nano Lett. 8, 2773-2778 (2008).
Yang et al. "Two-dimensional graphene nanoribbons." J. Am. Chem. Soc. 130, 4216-4217 (2008).
International Search Report and Written Opinion for PCT/US2012/055414, mailed on Nov. 20, 2012.
International Search Report and Written Opinion for PCT/US2010/038368, mailed on Aug. 13, 2010.
Office Action for U.S. Appl. No. 13/378,528, mailed on Apr. 11, 2014.
Office Action for U.S. Appl. No. 13/378,528, mailed on Jul. 29, 2014.
Huang et al., Making a field effect transistor on a single graphene nanoribbon by selective doping, Applied Physics Letters, 91, 253122 (2007).
Yazami et al., Self-organized carbon nanostrips with a new LiC10 structure derived from carbon nanotubes, Journal of Chemical Physics, 2001, 115(23):10585-10588.
Cano-Marquez et al., Ex-MWNTs: Graphene Sheets and Ribbons Produced by Lithium Intercalation and Exfoliation of Carbon Nanotubes, Nano Lett., vol. 9, No. 4, 2009, pp. 1527-1533.
International Preliminary Report on Patentability for PCT/US2010/038368, mailed on Dec. 29, 2011.
Office Action for Chinese Patent Application No. 201280044531.X, mailed on Feb. 13, 2015.
Kosynkin et al. "Highly Conductive Graphene Nanoribbons by Longitudinal Splitting of Carbon Nanotubes Using Potassium Vapor," ACS NANO 5, 968-974 (2011).
Novoselov et al., Electric Field Effect in Atomically Thin Carbon Films. Science 2004, 306, 666-669.
Li et al. Large-Area Synthesis of High-Quality and Uniform Graphene Films on Copper Foils. Science 2009, 324, 1312-1314.
Yu et al., Control and Characterization of Individual Grains and Grain Boundaries in Graphene Grown by Chemical Vapour Deposition. Nat. Mater. 2011, 10, 443-449.
Hummers et al., Preparation of Graphitic Oxide. J. Am. Chem. Soc. 1958, 80, 1339-1339.
Marcano et al., Improved Synthesis of Graphene Oxide. ACS Nano 2010, 4, 4806-4814.
Stankovich et al., Synthesis of Graphene-Based Nanosheets via Chemical Reduction of Exfoliated Graphite Oxide. Carbon 2007, 45, 1558-1565.
Lee et al., One-Step Exfoliation Synthesis of Easily Soluble Graphite and Transparent Conducting Graphene Sheets. Adv. Mater. 2009, 21, 4383-4387.
Stankovich et al., Graphene-Based Composite Materials. Nature 2006, 442, 282-286.
Jiao et al., Narrow Graphene Nanoribbons from Carbon Nanotubes. Nature 2009, 458, 877-880.
Bai et al., Rational Fabrication of Graphene Nanoribbons Using a Nanowire Etch Mask. Nano Letters 2009, 9, 2083-2087.
Sprinkle et al., Scalable Template Growth of Graphene Nanoribbons on SiC Nature Nanotech. 2010, 5, 727-731.
Elías et al., Longitudinal Cutting of Pure and Doped Carbon Nanotubes to Form Graphitic Nanoribbons Using Metal Clusters as Nanoscalpels Nano Letters 2010, 10, 366-372.
Yu et al., Strength and Breaking Mechanism of Multiwalled Carbon Nanotubes under Tensile Load Science 2000, 287, 637-640.
Luo et al. Chemical Approaches toward Graphene-Based Nanomaterials and their Applications in Energy-Related Areas. Small 2012, 8(5):630-646.
Wu et al., Graphenes as Potential Material for Electronics. Chem. Rev. 2007, 107, 718-747.
Becerril et al., Evaluation of Solution-Processed Reduced Graphene Oxide Films as Transparent Conductors. ACS Nano 2008, 2, 463-470.
Li et al., Highly conducting graphene sheets and Langmuir-Blodgett films. Nat. Nanotechnol. 2008, 3, 538-542.
Shih et al., Bi-and Trilayer Graphene Solutions. Nat. Nanotechnol. 2011, 6, 439-445.
Jiao et al., Facile Synthesis of High-Quality Graphene Nanoribbons. Nat. Nanotechnol. 2010, 5, 321-325.
Wang et al., Transition-Metal-Catalyzed Unzipping of Single-Walled Carbon Nanotubes into Narrow Graphene Nanoribbons at Low Temperature. Angew. Chem. Int. Ed. 2011, 50, 1-6.
Zhu et al., Rational Design of Hybrid Graphene Films for High-Performance Transparent Electrodes. ACS Nano 2011, 5, 6472-6479.
Ericson et al., Macroscopic, Neat, Single-Walled Carbon Nanotube Fibers. Science 2004, 305, 1447-1450.
Dimiev et al., Low-Loss, High-Permittivity Composites Made from Graphene Nanoribbons. ACS App. Mater. Interfaces 2011, 3, 4657-4661.
Genorio et al., In situ Intercalation Replacement and Selective Functionalization of Graphene Nanoribbon Stacks ACS Nano 2012, 6, 4231-4240.
Morelos-Gómez et al., Clean Nanotube Unzipping by Abrupt Thermal Expansion of Molecular Nitrogen: Graphene Nanoribbons with Atomically Smooth Edges ACS Nano 2012, 6, 2261-2272.
Chen et al., The Structural Evolution of Thin Multi-walled Carbon Nanotubes during Isothermal Annealing. Carbon, 2007, 45, 274-280.
Search Report and Written Opinion for Singapore Patent Application No. 2014014880, mailed on Jun. 22, 2015.
European Patent Office, Search Report dated Jul. 23, 2015 for Application No. EP12832239.3, "Solvent-Based Methods for Production of Graphene Nanoribbons", William Marsh Rice University, applicant.
Intellectual Property Office of Singapore, Second Written Opinion, Application No. 2014014880, Sep. 14, 2012.
The State Intellectual Property Office of the People's Republic of China, Notice on the second office action, Sep. 22, 2015, Application No. 201280044531.X.
The State Intellectual Property Office of the People'S Republic of China, Notice on the third office action, Mar. 21, 2016, Application No. 201280044531.X.
Russian Federation Patent Office, Official Action, Application No. 2014114285/05(022341), Jun. 9, 2016.

* cited by examiner

A

B

A

B

A

B

A

B

A

B

A

B

A

B

C

A

B

C

A

B

C

A

B

A

B

A

B

SOLVENT-BASED METHODS FOR PRODUCTION OF GRAPHENE NANORIBBONS

CROSS-REFERENCE TO RELATED APPLICATIONS

This application claims priority to U.S. Provisional Patent Application No. 61/534,553, filed on Sep. 14, 2011. This application is also related to PCT/US2010/038368. The entirety of each of the aforementioned applications is incorporated herein by reference.

BACKGROUND

Current methods of making graphene nanoribbons have numerous limitations in terms of efficiency, costs, yield, and quality. For instance, current methods may produce graphene nanoribbons in low quantities. Furthermore, the produced graphene nanoribbons may have numerous defects, limited dispersion in various solvents and composites, and limited conductivity. Therefore, a need exists for novel methods of efficiently producing graphene nanoribbons with minimal defects, enhanced dispersibility, and enhanced conductivity. There is also a need to have edge functionalized graphene nanoribbons to improve graphene nanoribbon dispersibility without sacrificing conductivity by disruption of the basal planes.

SUMMARY

In some embodiments, the present disclosure provides methods of preparing functionalized graphene nanoribbons. In some embodiments, such methods include: (1) exposing a plurality of carbon nanotubes to an alkali metal source in the presence of an aprotic solvent, wherein the exposing opens the carbon nanotubes; and (2) exposing the opened carbon nanotubes to an electrophile to form functionalized graphene nanoribbons. In some embodiments, such methods may also include a step of exposing the opened carbon nanotubes to a protic solvent in order to quench any reactive species on the opened carbon nanotubes and thereby leave protons (i.e., hydrogen atoms) on the edges.

Additional embodiments of the present disclosure pertain to methods of preparing unfunctionalized graphene nanoribbons by: (1) exposing a plurality of carbon nanotubes to an alkali metal source in the presence of an aprotic solvent to open the carbon nanotubes; and (2) exposing the opened carbon nanotubes to a protic solvent to form unfunctionalized graphene nanoribbons. In some embodiments, such methods may also include a step of functionalizing the graphene nanoribbons through electrophilic substitution reactions by adding an electrophile to the formed graphene nanoribbons.

In some embodiments, the methods of the present disclosure may take place at room temperature. In some embodiments, the methods of the present disclosure may utilize various types of carbon nanotubes, such as single-walled carbon nanotubes, double-walled carbon nanotubes, triple-walled carbon nanotubes, multi-walled carbon nanotubes, ultra-short carbon nanotubes, and combinations thereof. In some embodiments, the methods of the present disclosure may utilize multi-walled carbon nanotubes.

Various alkali metal sources may also be utilized to open the carbon nanotubes. In some embodiments, the alkali metal sources may include at least one of lithium, potassium, sodium, rubidium, caesium, alloys thereof, and combinations thereof. In some embodiments, the alkali metal sources may include potassium.

In addition, to optimize reaction conditions, the alkali metal sources of the present disclosure may be exposed to carbon nanotubes in the presence of various aprotic solvents. In some embodiments, the aprotic solvents may include at least one of diethyl ether, tetrahydrofuran, 1,4-dioxane, glyme, 1,2-dimethoxyethane, diglyme, tetraglyme, amines, N,N,N',N'-tetramethylethylenediamine, triethylamine, 1,4-diazabicyclo[2.2.2]octane, trialkylamines, dialkylarylamines, alkyldiarylamines, dimethylformamide, and combinations thereof.

Likewise, to quench any reactive species, the opened carbon nanotubes may be exposed to various protic solvents. In some embodiments, the protic solvents may include at least one of formic acid, n-butanol, isopropanol, n-propanol, ethanol, methanol, acetic acid, water, hydrochloric acid, sulfuric acid, ammonia, diethyl amine, dialkylamines, monoalkylamines, diarylamines, monoarylamines, monoalkymonoarylamines, and combinations thereof.

Moreover, various electrophiles may be utilized to form functionalized graphene nanoribbons. In some embodiments, the electrophiles may include at least one of water, alcohols, organic halides, alkenes, alkyl halides, acyl halides, allylic halides, benzyl halides, benzylic halides, alkenyl halides, aryl halides, alkynyl halides, fluoralkly halides, perfluoroalkyl halides, aldehydes, ketones, methyl vinyl ketones, esters, sulfonate esters, acids, acid chlorides, carboxylic acids, carboxylic esters, carboxylic acid chlorides, carboxylic acid anhydrides, carbonyl bearing compounds, enones, nitriles, carbon dioxide, halogens, monomers, vinyl monomers, ring-opening monomers, isoprenes, butadienes, styrenes, acrylonitriles, methyl vinyl ketones, methacrylates, 1,4-dimethoxy-2-vinylbenzene, methyl methacrylate, alkyl acrylates, alkyl methacrylates, trimethylsilyl chlorides, tert-butyldimethylsilyl chlorides, triphenylsilyl chlorides, epoxides, carbon dioxide, carbon disulfide, tert-butanol, 2-methylpropene, bromine, chlorine, iodine, fluorine, and combinations thereof.

In various embodiments, the electrophiles may be associated with transition metal catalysts, such as palladium-containing systems, nickel-containing systems, or iron-containing systems. In some embodiments, the electrophiles may not be associated with transition metal catalysts.

In some embodiments, the electrophile may include one or more monomers, such as olefins, vinyl monomers, styrenes, isoprenes, butadienes, acrylonitriles, methyl vinyl ketones, alkyl acrylates, alkyl methacrylates, ring opening monomers, epoxides, and combinations thereof. In some embodiments, the monomers may polymerize upon addition to graphene nanoribbons, thereby forming polymer-functionalized graphene nanoribbons.

In some embodiments, the methods of the present disclosure may also include a step of deintercalating functional groups from one or more layers of formed graphene nanoribbons. In some embodiments, deintercalation occurs by heating the formed graphene nanoribbons.

Further embodiments of the present disclosure pertain to graphene nanoribbons formed by the methods of the present disclosure. In some embodiments, the graphene nanoribbons may be edge-functionalized. In some embodiments, the graphene nanoribbons may include polymer-functionalized graphene nanoribbons. Additional embodiments of the present disclosure pertain to nanocomposites, fibers, displays, and circuits containing the aforementioned graphene nanoribbons.

The graphene nanoribbons of the present disclosure can have various advantageous properties, including good yield, minimal defects, enhanced dispersibility in various composites and solvents (e.g., organic solvents), and edge-functionalization without disruption of the graphene nanoribbon basal planes. The graphene nanoribbons formed in accordance with the methods of the present disclosure may also have enhanced conductivity, such as conductivities that range from about 0.1 S/cm to about 9,000 S/cm. Thus, the graphene nanoribbons of the present disclosure can find many mechanical and electrical applications.

BRIEF DESCRIPTION OF THE FIGURES

FIG. 2A illustrates the intercalation of potassium between the walls of MWNTs. FIG. 2B illustrates the splitting process of multi-walled carbon nanotubes (MWNTs) and formation of active carboanionic edges (M=$K^+$ or $Na^+$). FIG. 2C illustrates in-situ functionalization and intercalation of GNRs with alkyl groups. FIG. 2D illustrates the deintercalation of functionalized GNRs.

FIG. 3A shows an SEM image of pristine Mitsui MWNTs, and a 0.1 mg/mL suspension in chloroform. FIG. 3B shows pristine MWNTs from Nanotech Labs, Inc. (NTL) and a 0.1 mg/mL suspension in chloroform. FIG. 3C shows Mitsui-originated hexadecylated-GNRs (HD-GNRs) and a 0.1 mg/mL stable dispersion in chloroform. FIG. 3D shows NTL-originated HD-GNRs and a 0.1 mg/mL stable dispersion in chloroform.

FIG. 5A provides an SEM image of Mitsui-originated functionalized HD-GNRs. FIG. 5B provides an optical microscope of NTL-originated functionalized HD-GNRs.

FIG. 6A shows an SEM image of a device made from HD-GNR stacks that were NTL MWNTs-originated. Pt electrodes in the device are also shown. FIG. 6B shows change in electrical properties after different thermal treatment compared to as-prepared HD-GNRs.

FIG. 9A provides statistical representation of bulk conductivities of starting material MWNTs and functionalized HD-GNRs using a four-point probe cell. Five pellets of each sample were prepared. The pellets were pressed using a pellet die with a 13 mm diameter. 100 mg of sample was loaded into the die and pressed applying 8 T of pressure for 30 s. The solid pellet was then loaded into the four-point probe cell shown in FIG. 9B. Current and potential were then measured.

FIG. 13A shows comparison of as-prepared intercalated HD-GNRs and thermally treated HD-GNRs, where deintercalation is observed. FIG. 13B shows comparison of functionalized HD-GNRs, O-GNRs, B-GNRs, GNRs and MWNTs. Peaks at 21.8°, 25.3°, 35.9°, 42.4°, 44.4°, 51.8°, 56.8°, and 58.4° correspond to low concentrations of potassium iodide (KI) impurity.

FIG. 16A is a GC plot (purple curve) of trapped (at 0° C.) condensate from HD-GNRs heated at 150° C. in high vacuum for 1 hour. The concentration of the condensate contents was as follows: 45.1% dotriacontane, 35.1% hexadecane, 13.4% 1-iodohexadecane, and 6.4% hexadecene. Other minor components were disregarded. FIG. 16B is a GC plot (navy blue) of control reaction. The concentration of products was as follows: 59.6% dotriacontane, 20.8% hexadecene, and 19.6% hexadecane. The excess of 1-iodohexadecane (the major component) and other minor components were disregarded in calculating the percentages. FIG. 16C is a GC plot (wine red) of hexadecane standard. FIG. 16D is a GC plot (green) of 1-iodohexadecane standard.

FIG. 21A shows a step where MWNTs are intercalated with tetrahydrofuran (THF)-stabilized potassium naphthalenide (blue dots). FIG. 21B shows the longitudinal opening of the walls of the MWNTs due to expansion caused by intercalation of THF-stabilized potassium ions into MWNTs ($M^+$=$K^+$). FIG. 21C shows the addition of monomers (e.g., styrenes) to the opened MWNTs. The monomers assist in the further splitting and exfoliation of MWNTs (R: polystyrene). FIG. 21D shows the polymerization of the added monomers on the opened MWNTs and the subsequent formation of PF-GNRs upon quenching. For clarity, double bonds in the conjugated structure were omitted.

FIG. 24A is an SEM image showing the conversion of MWNTs to PF-GNRs through liquid-phase intercalation of Mitsui MWNTs with potassium naphthalenide followed by addition of styrene. FIG. 24B is a transmission electron microscope (TEM) image of the edge structure of multi-layered (5-layered) PF-GNRs.

FIG. 26A provides a 3D thermogravimetric mass spectrum (TG-MS) of the gas phase during the thermal degradation of PF-GNRs and MWNTs. Different colors represent gas products with different m/z, where m is the mass of the gas products and z is the charge. The black and gold curves correspond to the TGA profile of PF-GNRs and MWNTs, respectively. FIG. 26B shows Raman spectra of PF-GNRs and MWNTs. Disordered structure or defects were introduced onto PF-GNRs, owing to the splitting of MWNTs caused by intercalation followed by polymerization. FIG. 26C provides x-ray photoelectron spectroscopy (XPS) of GNRs. The inset is high-resolution XPS C1s spectrum of GNRs, indicating GNRs are free of oxidation.

FIG. 28A shows the polymerization of styrene in a flask, as initiated by potassium vapor treated MWNTs. FIG. 28B provides representative SEM images of split MWNTs. The majority of MWNTs were split. Ribbon-like structure could be indentified in the image. FIG. 28C provides a 3D plot of the TG-MS results of PF-GNRs and MWNTs. Different colors represent gas products with different m/z, where m is the mass of the gas products, and z is the charge. The black and gold curves correspond to the TGA profile of PF-GNRs and MWNTs, respectively.

FIG. 29A shows an SEM image of Mitsui MWNTs treated with potassium vapor followed by addition of isoprene. Most MWNTs are opened. However, they are not fully exfoliated to form GNRs. The ribbon-like structure and split MWNTs bridged by polymer byproducts can be observed. The highlighted portion represents a partially exfoliated MWNT on top of PF-GNR. FIG. 29B provides a TEM image of an isolated PF-GNR sitting on top of lacy carbon grid. FIG. 29C provides a TEM image of the edge structure of multi-stack PF-GNRs.

FIG. 30A is a low-magnification SEM image. FIG. 30B is a high-magnification SEM image. FIG. 30C is an SEM image of NTL MWNTs after liquid-phase intercalation followed by addition of styrene. It is shown that NTL MWNTs are split but not completely flattened.

FIG. 31A is an SEM image of pristine Baytubes. FIG. 31B is an SEM image of Baytubes after liquid-phase intercalation followed by polymerization. The image shows that the Baytubes are split due to intercalation followed by polymerization. However, most of the Baytubes remain intact.

FIG. 32A shows XRD patterns of Mitsui MWNTs, NTL MWNTs and Baytubes. The $d_{002}$ was calculated according to Bragg's equation: $\lambda=2d \sin \theta$, where λ is 1.54 Å for Cu Kα. FIG. 32B shows Raman spectra of Mitsui MWNTs, NTL MWNTs and Baytubes. Baytubes have the highest $I_D/I_G$, indicating most defective graphitic structure. Also present is the combination of G+D band induced by disordered structure, which is not observed in Mitsui MWNTs or NTL MWNTs.

FIG. 33A is an SEM image of MWNTs treated with sodium naphthalenide followed by styrene. FIG. 33B is an SEM image of MWNTs treated with lithium naphthalenide followed by styrene.

DETAILED DESCRIPTION

Figure 1:
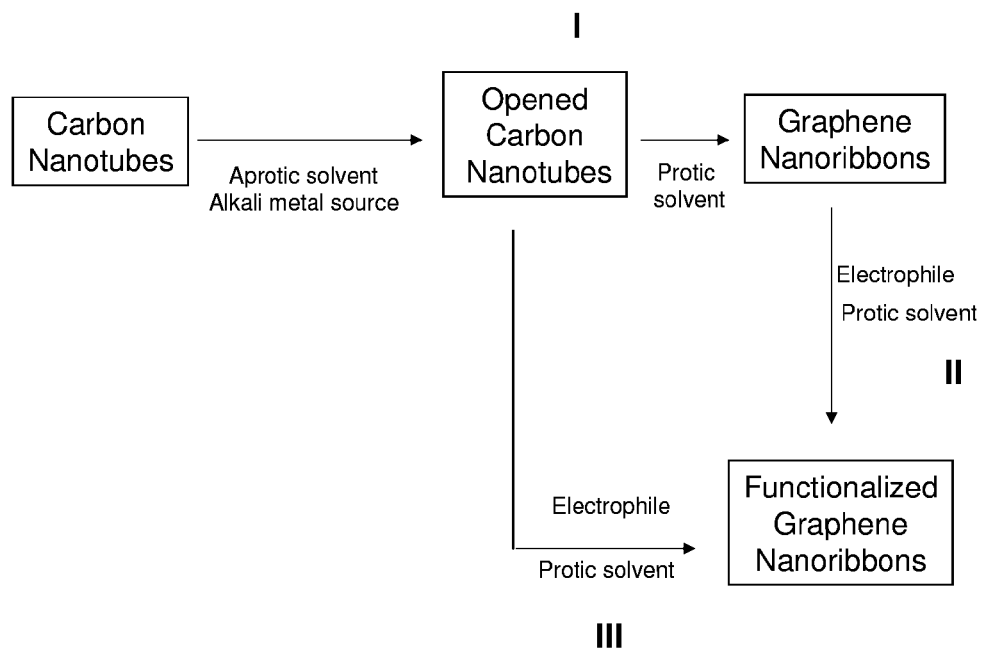
FIG. 1 provides various schemes for producing functionalized and unfunctionalized graphene nanoribbons (GNRs).

It is to be understood that both the foregoing general description and the following detailed description are illustrative and explanatory, and are not restrictive of the subject matter, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

The section headings used herein are for organizational purposes and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

Graphene nanoribbons (GNRs) exhibit unique electronic, mechanical and thermal properties. Several lithographic, chemical, and synthetic procedures have been reported to produce GNRs at the nanoscale and microscale levels. Macroscopic quantities of GNRs can also be prepared by using either high temperatures, low temperatures, or oxidation/reduction protocols. The first two methods require high energy input, thereby resulting in excessive costs. The third method yields defective GNRs with limited conductivity, especially when incorporated into various materials.

Furthermore, the dispersion of GNRs into various composites has numerous limitations. For instance, polymer/graphene nanocomposites are mainly prepared by mixing reduced graphene oxide with different polymer matrices. Such chemically converted graphenes can be well dispersed in polymer matrices due to their residual oxygen containing groups. However, the conductivity of polymers cannot be remarkably improved since the conjugated structure of graphene cannot be completely restored, even after chemical reduction.

Moreover, the reinforcement of graphene cannot be fully realized due to defects introduced during oxidation. For instance, defects or holes on graphene basal planes could serve as seed points for crack initiation. In addition, during the reduction of graphene oxide, large amounts of gases can evolve and weaken the composite through gas flow.

Thus, a need exists for the development of improved methods for producing GNRs that are cost effective. Furthermore, a need exists for producing GNRs that are substantially free of defects. A need also exists for producing GNRs that are conductive and dispersible in various solvents and composites. The present disclosure addresses the aforementioned needs.

In particular, the present disclosure provides various methods of producing functionalized and unfunctionalized GNRs. Additional embodiments of the present disclosure pertain to the formed GNRs, and composites, fibers, displays, and circuits containing the formed GNRs.

Methods of Producing GNRs

Various embodiments of methods of producing GNRs are illustrated in FIG. 1. For instance, in some embodiments that are illustrated in Panel I of FIG. 1, the present disclosure provides methods of preparing unfunctionalized GNRs. Such methods generally include: (1) exposing a plurality of carbon nanotubes to an alkali metal source in the presence of an aprotic solvent to longitudinally open the carbon nanotubes; and (2) exposing the opened carbon nanotubes to a protic solvent to quench any reactive species and form unfunctionalized GNRs (i.e., GNRs with protons at the edges).

Additional embodiments of the present disclosure pertain to methods of producing functionalized GNRs by a multi-step method, as illustrated in Panels I and II of FIG. 1. Such methods generally include: (1) exposing a plurality of carbon nanotubes to an alkali metal source in the presence of an aprotic solvent to open the carbon nanotubes; (2) exposing the opened carbon nanotubes to a protic solvent to quench any reactive species and form unfunctionalized GNRs; and (3) functionalizing the GNRs through electrophilic substitution reactions by exposing the GNRs to one or more electrophiles. In some embodiments, the functionalizing step may occur in the presence of a promoter, such as a Lewis acid.

Further embodiments of the present disclosure pertain to methods of producing functionalized GNRs through an in situ or "one-pot" reaction, where GNRs are produced and functionalized under the same reaction conditions. Embodiments of such methods are illustrated in Panels I and III of FIG. 1. Such methods generally include: (1) exposing a plurality of carbon nanotubes to an alkali metal source in the presence of an aprotic solvent to open the carbon nanotubes; and (2) exposing the opened carbon nanotubes to an electrophile to form functionalized graphene nanoribbons. In some embodiments, such methods may also include an additional step of exposing the functionalized GNRs to a protic solvent in order to quench any remaining reactive species.

As set forth in more detail herein, the methods of the present disclosure can have numerous variations. For instance, various carbon nanotubes, alkali metal sources, aprotic solvents, protic solvents and electrophiles may be utilized in various embodiments of the present disclosure.

Carbon Nanotubes

The graphene nanoribbons of the present disclosure may be derived from various carbon nanotubes. In some embodiments, the carbon nanotubes may include at least one of single-walled carbon nanotubes, double-walled carbon nanotubes, triple-walled carbon nanotubes, multi-walled carbon nanotubes, ultra-short carbon nanotubes, and combinations thereof. In some embodiments, the carbon nanotubes include multi-walled carbon nanotubes.

Furthermore, the utilized carbon nanotubes may be in various states. For instance, in some embodiments, the carbon nanotubes may be in pristine or unfunctionalized form. In some embodiments, the carbon nanotubes may be functionalized with one or more functional groups, such as carboxyl groups, alkyl groups, esters, aryl groups, polymers, and the like.

Alkali Metal Sources

Alkali metal sources generally refer to compounds that include one or more alkali metals, such as metals from Group 1 of the periodic table of elements. In some embodiments, the alkali metal source may include at least one of lithium, potassium, sodium, rubidium, caesium, alloys thereof, and combinations thereof. In some embodiments, the alkali metal source may include potassium. In some embodiments, the alkali metal source may include a sodium/potassium (Na/K) alloy, potassium naphthalenide, sodium naphthalenide, lithium naphthalenide, mixtures of potassium and naphthalene, and combinations thereof. In some embodiments, the alkali metal is potassium or a mixture of potassium and another metal.

The alkali metal sources of the present disclosure may be applied to carbon nanotubes in various states. In some embodiments, the alkali metal sources may be in a vapor or gaseous state. In some embodiments, the alkali metal sources may be in a liquid state. In some embodiments, the alkali metal sources may be in gaseous and liquid states. In some embodiments, the alkali metal sources may include molten alkali metals. In some embodiments, the alkali metal sources may include alkali metal vapors. In some embodiments, the alkali metal vapors may be produced from molten alkali metals.

Without being bound by theory, it is envisioned that alkali metal sources facilitate the formation of graphene nanoribbons by reacting with and opening the carbon nanotubes. See, e.g., FIGS. 2 and 21. In some embodiments, the alkali metal sources may longitudinally open or split the carbon nanotubes. See, e.g., FIGS. 2A and 21B.

In some embodiments, alkali metal sources intercalate between the carbon nanotubes to affect their longitudinal opening. Without again being bound by theory, it is envisioned that the intercalation of various solvent-stabilized alkali metal sources into carbon nanotubes may lead to expansion of the d-space between carbon nanotube layers, thereby causing the carbon nanotubes to partially open.

In some embodiments, the carbon nanotubes are opened from a site that is parallel to their longitudinal axis. In some embodiments, the longitudinal opening of carbon nanotubes may involve a straight bond opening process along the sidewall of the carbon nanotube, paralleling but not crossing the longitudinal axis. In some embodiments, the longitudinal opening of carbon nanotubes may involve a predominantly spiral-wise opening of the carbon nanotubes, again paralleling but not crossing the longitudinal axis.

In some embodiments, the opening of carbon nanotubes by alkali metal sources may be facilitated by heating. For instance, in some embodiments, the reaction may be heated to about 100° C.-400° C. to facilitate the opening of carbon nanotubes by alkali metal sources. In some embodiments, the opening may occur at room temperature.

Furthermore, the alkali metal sources of the present disclosure may become associated with carbon nanotubes and GNRs through various interactions. Such interactions may involve covalent interactions, non-covalent associations, and ionic interactions. For instance, in some embodiments, the alkali metal sources may become covalently or ionically bound to the opened carbon nanotubes before an electrophile or a protic solvent is added. In some embodiments, the alkali metal sources may become covalently or ionically bound to the edges of the opened carbon nanotubes or formed graphene nanoribbons. In some embodiments, the alkali metal sources may become covalently or ionically bound to both the edges and the basal planes of the opened carbon nanotubes or formed graphene nanoribbons. In some embodiments, the alkali metal sources may result in the formation of active carboanionic moieties on the opened carbon nanotubes or formed graphene nanoribbons. See, e.g., FIG. 2B.

Aprotic Solvents

The alkali metal sources of the present disclosure may be applied to carbon nanotubes in the presence of various solvents, such as aprotic solvents. Aprotic solvents generally refer to solvents that lack an acidic hydrogen. Without being bound by theory, it is envisioned that the use of aprotic solvents facilitates the opening of carbon nanotubes by alkali metal sources by providing a non-reductive environment that in turn facilitates the formation of reactive alkali species.

Various aprotic solvents may be utilized in the methods of the present disclosure. In some embodiments, the aprotic solvents may include, without limitation, diethyl ether, tetrahydrofuran (THF), 1,4-dioxane, glyme, 1,2-dimethoxyethane (DME), diglyme, tetraglyme, N,N,N',N'-tetramethylethylenediamine, triethylamine, 1,4-diazabicyclo[2.2.2]octane (DABCO), trialkylamines, dialkylarylamines, alkyldiarylamines, dimethylformamide, and combinations thereof. In some embodiments, the aprotic solvents may include polar aprotic solvents, ethereal solvents, amines, or other solvents capable of facilitating the formation of reactive alkali species.

The aprotic solvents of the present disclosure may also be in various states. In some embodiments, the aprotic solvents may be in anhydrous form, in degassed form, or combinations of such forms. In some embodiments, the aprotic solvents may be in anhydrous and degassed forms.

Protic Solvents

After carbon nanotubes are opened by alkali metal sources, they may be exposed to one or more protic solvents. Protic solvents generally refer to solvents that contain one or more dissociable hydrogen atoms. In some embodiments, the protic solvents of the present disclosure may have a $pK_a$ of about 35 or less. Without being bound by theory, it is envisioned that protic solvents can quench any reactive species on the formed graphene nanoribbons.

In some embodiments, the protic solvents may include, without limitation, formic acid, n-butanol, isopropanol, n-propanol, ethanol, methanol, acetic acid, water, hydrochloric acid, sulfuric acid, ammonia, diethylamine, dialkylamines, monoalkylamines, diarylamines, monoarylamines, monoalkymonoarylamines, and combinations thereof. In some embodiments, the protic solvents may include polar protic solvents, such as methanol.

In some embodiments, the protic solvents may include one or more $R_2NH$ groups, one or more $RNH_2$ groups, or combinations thereof. In some embodiments, the R groups may include an alkyl group, an aryl group, or combinations thereof. Additional protic solvents can also be envisioned.

In some embodiments, the exposure of carbon nanotubes to protic solvents may occur during or after exposure of carbon nanotubes to alkali metal sources. See, e.g., Panel I in FIG. 1. In some embodiments, the exposure of carbon nanotubes to protic solvents may occur during or after exposure of opened carbon nanotubes to one or more electrophiles. See, e.g., Panel III in FIG. 1.

Electrophiles

Electrophiles generally refer to compounds that can react with electron rich centers. In some embodiments, carbon nanotubes that have been treated with alkali metals may react in situ with electrophiles to form functionalized graphene nanoribbons. See, e.g., FIG. 1, Panel III. In some embodiments, graphene nanoribbons that have already been formed may react with electrophiles through electrophilic substitution reactions to form functionalized graphene nanoribbons. See, e.g., FIG. 1, Panel II. In some embodiments, the electrophiles may quench excess alkali metal sources and functionalize the graphene nanoribbons with various functional groups (e.g., organic functional groups, such as halogens or hydrogen). In some embodiments, the electrophiles may functionalize graphene nanoribbons by displacing alkali metal sources on the graphene nanoribbons with functional groups.

Various electrophiles may be used to functionalize graphene nanoribbons. In some embodiments, the electrophiles may include, without limitation, water, alcohols, organic halides and synthetic equivalents thereof, alkenes, alkyl halides, acyl halides, allylic halides, benzyl halides, benzylic halide, alkenyl halides, aryl halides, alkynyl halides, fluoralkly halides, perfluoroalkyl halides, aldehydes, ketones, methyl vinyl ketones, esters, sulfonate esters, acids, acid chlorides, carboxylic acids, carboxylic esters, carboxylic acid chlorides, carboxylic acid anhydrides, carbonyl bearing compounds, enones, nitriles, carbon dioxide, halogens, monomers, vinyl monomers, ring-opening monomers, isoprenes, butadienes, styrenes, acrylonitriles, methyl vinyl ketones, methacrylates, 1,4-dimethoxy-2-vinylbenzene, methyl methacrylate, alkyl acrylates, alkyl methacrylates, trimethylsilyl chlorides, tert-butyldimethylsilyl chlorides, triphenylsilyl chlorides, epoxides, carbon dioxide, carbon disulfide, tert-butanol, 2-methylpropene, C60, C70, bromine, chlorine, iodine, fluorine and combinations thereof.

In various embodiments, the electrophiles may be associated with transition metal catalysts, such as palladium-containing systems, nickel-containing systems, or iron-containing systems. Exemplary electrophiles that may be associated with transition metal catalysts may include, without limitation, aryl halides, alkenyl halides, alkynyl halides, and combinations thereof. In some embodiments, the electrophiles may not be associated with transition metal catalysts.

In some embodiments, the electrophiles may include alkanes, such as haloalkanes and iodoalkanes. In some embodiments, the electrophiles may include iodoalkanes, such as 1-iodohexadecane, 1-iodooctane, and 1-iodobutane.

In some embodiments, the electrophiles may include one or more polarized neutral molecules, such as alkyl halides, acyl halides, carbonyl bearing compounds, epoxides, and the like. In some embodiments, the electrophiles may include one or more polarizable neutral molecules, such as fluorine, chlorine, bromine, iodine, styrenes, dienes, and the like.

In some embodiments, the electrophiles may be a proton donor, such as, for example, an alcohol or water. In other embodiments, the electrophiles may be organic halides (e.g, alkyl halide, aryl halide, benzylic halide, allylic halide, alkenyl halide, alkynyl halide or perfluoroalkyl halide) or synthetic equivalents of organic halides (e.g., a sulfonate ester). In still other embodiments, the electrophiles may be halogens (e.g., fluorine, chlorine, bromine or iodine), carbon dioxide, carboxylic acids, carboxylic esters, carboxylic acid chlorides, carboxylic acid anhydrides, aldehydes, ketones, enones, or nitriles. In some embodiments, the electrophile is carbon dioxide.

In some embodiments, the electrophiles may be monomers. In some embodiments, the monomers may include at least one of olefins, vinyl monomers, styrenes, isoprenes, butadienes, acrylonitriles, methyl vinyl ketones, alkyl acrylates (e.g., methyl acrylate or ethyl acrylate), alkyl methacrylates (e.g., methyl methacrylate or ethyl methacrylate), ring opening monomers, (e.g., lactones or lactams), epoxides, and combinations thereof.

In various embodiments, monomeric electrophiles can be used to form polymer-functionalized graphene nanoribbons (PF-GNRs) and polymer/graphene nanoribbon composites. In particular, it has been demonstrated that monomeric electrophiles can polymerize upon exposure to opened carbon nanotubes or graphene nanoribbons that have been treated with alkali metal sources. See, e.g., FIG. 21. For instance, through an in-situ reaction, alkali metal sources can open carbon nanotubes and initiate the polymerization of monomeric electrophiles at the same time. Furthermore, it is envisioned that polymerization may occur by various mechanisms, including radical polymerization and anionic polymerization.

In some embodiments, the electrophiles may include ring-opening monomers, such as, for example, epoxides (e.g., ethylene oxide), lactones or lactams. In some embodiments, the electrophiles may include vinyl monomers. Vinyl monomers may be added to carbon nanotubes before, during or after the addition of alkali metal sources. Without being bound by theory, it is envisioned that vinyl monomers have free vinyl groups that are available for polymerization once the monomers become bound to the formed graphene nanoribbons.

The use of additional electrophiles may also be envisioned. For instance, electrophiles may include any reagents capable of reacting with organometallic compounds of alkali metals and provide functional products with carbanions. In more specific embodiments, the electrophile may displace the alkali metal from the graphene nanoribbons and introduce a plurality of functional groups to the functionalized graphene nanoribbons. In some embodiments, the electrophile may be reacted under electrophilic aromatic substitution conditions through quenching a potassium intercalation compound with electrophiles or unsaturated hydrocarbons in a solvent.

In some embodiments, particularly where the electrophile is added through electrophilic substitution reactions, the addition may occur by halogenation, bromination, alkylation, tert-butylation, such as through the use of tert-butanol or isobutylene, and other similar reactions. In some embodiments, such electrophilic substitution reactions may be assisted by one or more Lewis acids, such as aluminum chloride or zinc chloride, or with one or more Bronsted acids, such as sulfuric acid or trifluoroacetic acid.

Exfoliation

In various embodiments, the graphene nanoribbons that are formed by the methods of the present disclosure may undergo additional treatments. For instance, in some embodiments, the formed graphene nanoribbons may undergo an exfoliation step to remove one or more layers of graphene from the formed graphene nanoribbons. In some embodiments, the exfoliation may result in the formation of single-layer GNRs, few-layer GNRs (i.e., 2-10 layers), or multi-layer GNRs (i.e., about 50 layers).

In some embodiments, the exfoliation may occur by exposing the graphene nanoribbons to a superacid solvent, such as Bronsted superacids, Lewis superacids, and conjugate Bronsted-Lewis superacids. In some embodiments, the superacids may include, without limitation, perchloric acid, chlorosulfonic acid, fluorosulfonic acid, trifluoromethanesulfonic acid, perfluoroalkane sulfonic acids, antimony pentafluoride, arsenic pentafluoride, fuming sulfuric acids, and combinations thereof. In some embodiments, the superacid may be chlorosulfonic acid. In some embodiments, the exfoliation may occur by exposing the graphene nanoribbons to a strong acid, such as concentrated sulfuric acid.

In some embodiments, the exfoliation step may include exposure of the graphene nanoribbons to a gas. In some embodiments, the gas may include a volatile gas. In some embodiments, the gas may include, without limitation, carbon dioxide, nitrogen gas, hydrogen gas, pentanes, hydrogen chloride, air, gases derived from a reaction of a diazonium compound, and combinations thereof. In some embodiments, the gas is carbon dioxide, such as carbon dioxide derived from a salt (e.g., $Na_2CO_3$) or dry ice. In some embodiments, the gas is hydrogen chloride, such as hydrogen chloride generated from sodium chloride and sulfuric acid. In some embodiments, the gas is nitrogen gas, such as nitrogen gas derived from liquid nitrogen.

Intercalation

In some embodiments, the methods of the present disclosure may also include an intercalation step. In some embodiments, intercalation occurs when various molecules become intercalated between layers of formed graphene nanoribbons. For instance, in some embodiments, intercalated alkali metals (e.g., potassium) and electrophiles (e.g., 1-iodoalkane) become positioned between graphene sheets. The by-product (e.g., KI) is forced out, while newly formed functional groups (e.g., alkanes, alkenes and alkyl groups) take their places between graphene sheets.

Defunctionalization

In some embodiments, the formed graphene nanoribbons of the present disclosure may also undergo a defunctionalization step, where the functional groups on the formed graphene nanoribbons are removed. In some embodiments, the defunctionalization step may include a thermal defunctionalization process. In some embodiments, the thermal defunctionalization process may involve heating the graphene nanoribbons at temperatures that range from about 100° C. to about 900° C.

Deintercalation

In some embodiments, the formed graphene nanoribbons of the present disclosure may also undergo a deintercalation step, where intercalated functional groups are removed from between the formed graphene layers. See, e.g., FIG. 2D. In some embodiments, deintercalation may occur by heating the GNRs at high temperatures. In some embodiments, the heating may occur at temperatures that range from about 100° C. to about 900° C., or from about 240° C. to about 900° C., or from about 530° C. to about 900° C. In some embodiments, the deintercalation step may last anywhere from about 20 minutes to about for 12 hours.

Reaction Conditions

The methods of the present disclosure may occur under various reactions conditions. For instance, in some embodiments, the methods of the present disclosure may occur under vacuum or an inert atmosphere. In some embodiments, the methods of the present disclosure may occur in an inert atmosphere, such as atmospheres under a steady stream of an inert gas (e.g., Ar, $H_2$, and the like). In some embodiments, the methods of the present disclosure may take place in the absence of any oxidants. In some embodiments, the starting products may undergo multiple freeze-thaw-pump cycles in order to remove oxygen.

The methods of the present disclosure may also take place at various temperatures. For instance, in some embodiments, the methods of the present disclosure may take place at room temperature. In some embodiments, the methods of the present disclosure may take place at temperatures that range from about 50° C. to about 500° C., or from about 250° C. and about 300° C.

In some embodiments, the formed graphene nanoribbons may be isolated or purified by various additional steps, such as filtration, centrifugation, washing with solvents suitable for the removal of expected impurities, drying, and other similar methods.

Derived Graphene Nanoribbons and Composites

Additional embodiments of the present disclosure pertain to graphene nanoribbons formed by the methods of the present disclosure. Further embodiments of the present disclosure pertain to composites, fibers, displays, and circuits containing such graphene nanoribbons. In some embodiments, the methods of the present disclosure may be used to make defect free and functionalized graphene nanoribbons.

In some embodiments, the graphene nanoribbons may only be functionalized on the edges, not the basal planes (i.e., edge-functionalized). In some embodiments, edge-functionalized GNRs may include, without limitation, alkyl-functionalized GNRs, such as hexadecylated-GNRs (HD-GNRs), octylated-GNRs (O-GNRs) and butylated-GNRs (B-GNRs). In some embodiments, the edge-functionalized GNRs may include polymer-functionalized GNRs.

In some embodiments, the GNRs formed by the methods of the present disclosure may be in single layers, few layers (e.g., 2-10), or multiple layers (e.g., more than 10-50 layers). In some embodiments, the GNRs may be intercalated with various functional groups, such as alkanes.

In more specific embodiments, the present disclosure pertains to composites or fibers that contain graphene nanoribbons. In some embodiments, the graphene nanoribbons are edge-functionalized. In some embodiments, the edge-functionalized graphene nanoribbons contain unfunctionalized basal planes.

In some embodiments, the graphene nanoribbons in the composites and fibers are edge-functionalized with polymers, such as polystyrenes, polyisoprenes, polybutadienes, polyacrylonitriles, polymethyl vinyl ketones, poly alkyl acrylates, polyalkyl methacrylates, polyols, and combinations thereof.

In some embodiments, the graphene nanoribbons in the composites and fibers are edge-functionalized with one or more functional groups, such as alkyl groups, acyl groups, allylic groups, benzyl groups, benzylic groups, alkenyl groups, aryl groups, alkynyl groups, fluoralkly groups, perfluoroalkyl groups, aldehydes, ketones, methyl vinyl ketones, esters, sulfonate esters, carboxyl groups, carbonyl groups, halogens, and combinations thereof. In more specific embodiments, the edge-functionalized graphene nanoribbons may include alkyl-functionalized graphene nanoribbons, hexadecylated graphene nanoribbons, octylated graphene nanoribbons, butylated graphene nanoribbons, and combinations thereof.

In some embodiments, the composites and fibers of the present disclosure can be utilized as components of various devices. Exemplary devices include, without limitation, transparent conductive displays, de-icing circuits, gas barrier composites, screens, and combinations thereof.

Applications and Advantages

The methods of the present disclosure can be used to make graphene nanoribbons with various advantageous properties, including good yield, minimal defects, and enhanced dispersability in various composites, polymers, plastics, rubbers, elastomers and solvents (e.g., organic solvents). Furthermore, since the starting products used to make the graphene nanoribbons of the present disclosure are accessible and inexpensive, the methods of the present disclosure can be used to make graphene nanoribbons in a cost-effective manner.

The graphene nanoribbons formed in accordance with the methods of the present disclosure may also have enhanced conductivity. For instance, in some embodiments, the graphene nanoribbons may have conductivities that range from about 0.1 S/cm to about 9,000 S/cm. In some embodiments, conductivity of the graphene nanoribbons may be about 4300 S/cm. In some embodiments, the conductivity of the graphene nanoribbons may be about 8,000 S/cm.

In view of the aforementioned advantageous properties, the graphene nanoribbons of the present disclosure can find many mechanical and electrical applications. For instance, due to minimal defects, the graphene nanoribbons of the present disclosure can be particularly advantageous for applications relying on mechanical strength such as, for example, polymer composites. In some embodiments, polymer functionalized graphene nanoribbons of the present disclosure may be incorporated into plastic composites, rubber composites and elastomer composites. In such embodiments, having a majority or all the polymer strands covalently bonded to a GNR can greatly increase the mechanical properties of the final article.

In some embodiments, the graphene nanoribbons of the present disclosure may be used as components of carbon fibers, membrane filters for gas separation or removal of particulates, reinforcement fillers for organic and inorganic composite materials, and additives for improving barrier properties of polymer matrices. In more specific embodiments, the graphene nanoribbons of the present disclosure may be used to improve gas barrier properties, such as in gas tanks and pipes for gases. Furthermore, the graphene nanoribbons of the present disclosure may be used as conductive films, semi-conductive films, touch-screen displays, de-icing circuits, batteries, electroactive materials, capacitors, solar cells, and precursors of cathode materials for lithium ion or lithium polymer batteries.

In some embodiments, the graphene nanoribbons of the present disclosure may also find applications in wound care. For instance, in some embodiments, the graphene nanoribbons of the present disclosure may be grafted or bonded to at least one anti-microbial agent. Such grafted graphene nanoribbon compositions may be included as part of a wound dressing to advantageously improve infection suppression, provide odor control, or inhibit lipophilic toxins from entering the wound. For example, in a non-limiting embodiment, graphene nanoribbons that have been grafted or bonded to at least one antimicrobial agent may be added to ordinary gauze.

Additional Embodiments

Reference will now be made to more specific embodiments of the present disclosure and experimental results that provide support for such embodiments. However, Applicants note that the disclosure below is for illustrative purposes only and is not intended to limit the scope of the claimed subject matter in any way.

EXAMPLE 1

Preparation of Non-functionalized Graphene Nanoribbons

In this Example, an exemplary protocol is provided for making non-functionalized graphene nanoribbons (GNRs) in accordance with the scheme illustrated in Panel I of FIG. 1. In this Example, multi-walled carbon nanotubes (MWNTs) are dispersed in an anhydrous and degassed polar aprotic solvent, preferably 1,2-dimethoxyethane or tetrahydrofuran. Thereafter, a potassium/naphthalene mixture or a sodium/potassium alloy is added to the mixture. This is followed by stirring at room temperature for hours or days. Next, excessive amounts of a protic solvent (preferably methanol) is added. The formed graphene nanoribbons are then isolated by filtration, centrifugation or any other suitable method of separation. This is accompanied by washing with solvents suitable for the removal of expected impurities. The product is then dried.

EXAMPLE 2

Functionalization of Graphene Nanoribbons from Example 1

In this Example, an exemplary protocol is provided for functionalizing the graphene nanoribbons from Example 1, in accordance with the scheme illustrated in Panel II of FIG. 1. The non-functionalized graphene nanoribbons obtained from Example 1 are dispersed in a mixture of an acid and an electrophile, preferably trifluoroacetic acid and tert-butanol or 2-methylpropene. The mixture is then stirred at boiling temperature. Next, the functionalized graphene nanoribbons are isolated by filtration, centrifugation or any other suitable method of separation. This is accompanied by washing with solvents suitable for the removal of expected impurities. The product is then dried.

EXAMPLE 3

In Situ Preparation of Functionalized Graphene Nanoribbons

In this Example, an exemplary protocol is provided for preparing functionalized graphene nanoribbons through an in situ (i.e., "one-pot") reaction, in accordance with the scheme illustrated in Panels I and III of FIG. 1. MWNTs are dispersed in an anhydrous and degassed polar aprotic solvent, preferably 1,2-dimethoxyethane or tetrahydrofuran. Next, a potassium/naphthalene or sodium/potassium alloy mixture is added. Thereafter, the mixture is stirred at room temperature for hours or 3 days. An excessive amount of an electrophile is then added. The mixture is then stirred for additional hours or 1 day. Next, an excessive amount of a protic solvent, preferably methanol, is added. The functionalized graphene nanoribbon is then isolated by filtration, centrifugation or other suitable methods. This is accompanied by washing with solvents suitable for the removal of expected impurities. The product is then dried.

In the aforementioned Examples, the chemicals used are fairly inexpensive. Furthermore, the chemicals can be easily recycled or converted to non-toxic products suitable for safe disposal. In addition, the isolation and purification of the graphene nanoribbons may require vacuum and inert atmosphere equipment. For instance, Na/K alloy is highly reactive with water and may catch on fire when exposed to air. Therefore, Na/K alloys must be handled with special precautions, preferably in a glove box. Quantities as small as one gram can be a fire or explosion risk. Additional protocols and conditions are disclosed in PCT/US2010/038368.

EXAMPLE 4

In-situ Intercalation Replacement and Selective Functionalization of Graphene Nanoribbon Stacks This Example provides a cost-effective and potentially industrially scalable, in-situ functionalization procedure for preparation of soluble GNRs from commercially available carbon nanotubes. The physical characteristics of the functionalized product were determined using SEM, evolved gas analysis, X-ray diffraction, solid-state $^{13}C$ NMR, Raman spectroscopy, and GC-MS analytical techniques. A relatively high preservation of electrical properties in the bulk material was observed. Moreover, replacement of intercalated potassium with haloalkanes was obtained. While carbon nanotubes can be covalently functionalized, the conversion of the sp²-hybridized carbon atoms to sp³-hybridized atoms dramatically lowers their conductivity. However, edge functionalized GNRs permit their heavy functionalization while leaving the basal planes intact.

Graphene is a stable 2D material that holds great promise due to its optimal electrical, mechanical, and thermal properties. For instance, graphene is a potential building block for electronic devices. The abundance of carbon and its low toxicity are additional driving forces for the scientific community to search for applications of graphene in energy-related devices such as ultra capacitors, Li-ion batteries, solar cells and for catalysis. However, two important issues need to be solved to realize the use of graphene and its derivatives in those future applications: a) bulk preparation of high quality graphene-based nanomaterials and b) functionalization and incorporation of these materials into devices.

Since the discovery of graphene in 2004, many different methods have been developed to yield graphene nanomaterials. These methods can be divided into bottom-up and top-down strategies. Bottom-up strategies include chemical vapor deposition (CVD) growth and organic synthesis. Both methods can deliver high quality and relatively low defect materials. However, such methods are hard to scale-up and process. On the other hand, there is scalable top-down approach where graphite or carbon nanotubes (CNTs) are used as a starting material. The most common preparation method of bulk-quantity graphene is by exfoliation of oxidized graphite with subsequent reduction or high temperature annealing to produce more highly conjugated materials. The disadvantage of this method is the irreversible damage to the graphene basal plane and its consequently lower conductivity.

High quality monolayer to few-layer graphene has been obtained in bulk quantities using different intercalation and thermal expansion techniques. When tuning the physical properties and minimizing defects, one must also consider the shape of the material that is inherently governed by the graphite precursor for top-down approaches.

It was reported that the width and edges of the graphene play important roles in defining the material's electronic properties. CNTs are known precursors for production of bulk quantities of well-defined graphene nanoribbons (GNRs). To date, several unzipping methods with reasonable yields have been reported. Due to their high carbon aspect ratio, which is advantageous for mechanical processing, GNRs are good candidates for applications in energy related devices, catalysis, transparent touch screens, carbon fiber spinning, formation of conductive polymer composites, and low-loss-high-permittivity composites. When dealing with applications, it is desirable for GNRs to be available in bulk quantities that are processable, especially since most of the applications require preparation of well-dispersed solutions or suspensions. Pristine graphene materials are very difficult to disperse, thus functionalization is generally required.

Layered carbon materials such as graphite or MWNTs are stable because of their fully π-conjugated aromatic system. Traditional organic synthetic approaches are thus limited to certain reactions. Polycyclic aromatic hydrocarbons (PAHs), close chemical relatives to graphene-based materials, are susceptible to electrophilic substitutions, nucleophilic and free radical reactions, addition reactions, reductions, oxidations and rearrangements. All of these reactions could be used for functionalization of graphene. However, the current graphene literature reports are limited mostly to oxidation, hydrogenation and reductive functionalization methods. These methods generally produce a product with the desired physical properties such as solubility and dispersability. The degree of functionalization in these cases is relatively high, mostly because the basal planes are functionalized. However, functionalization of the basal plane inevitably leads to a suppressed conductivity as the π-conjugation is disturbed. Selective edge functionalization might be a solution to this problem. However, edge functionalization would likely only have an impact on physical properties in materials with high edge-to-basal plane carbon ratios such as in GNRs.

In the present Example, Applicants further investigate the hypothesis that potassium intercalation between the walls of commercial multiwalled carbon nanotubes (MWNTs) would longitudinally split the walls and furnish active carboanionic edges on the ribbons. The increased reactivity of the edges compared to the basal plane would therefore preferably functionalize the edges of GNRs with desired electrophiles. Selective functionalization would introduce improved solubility without sacrificing conductivity. Further, Applicants investigated the replacement of intercalated metal with haloalkanes that then serve as intercalents in the resulting functionalized GNRs.

Results and Discussion

Figure 2:
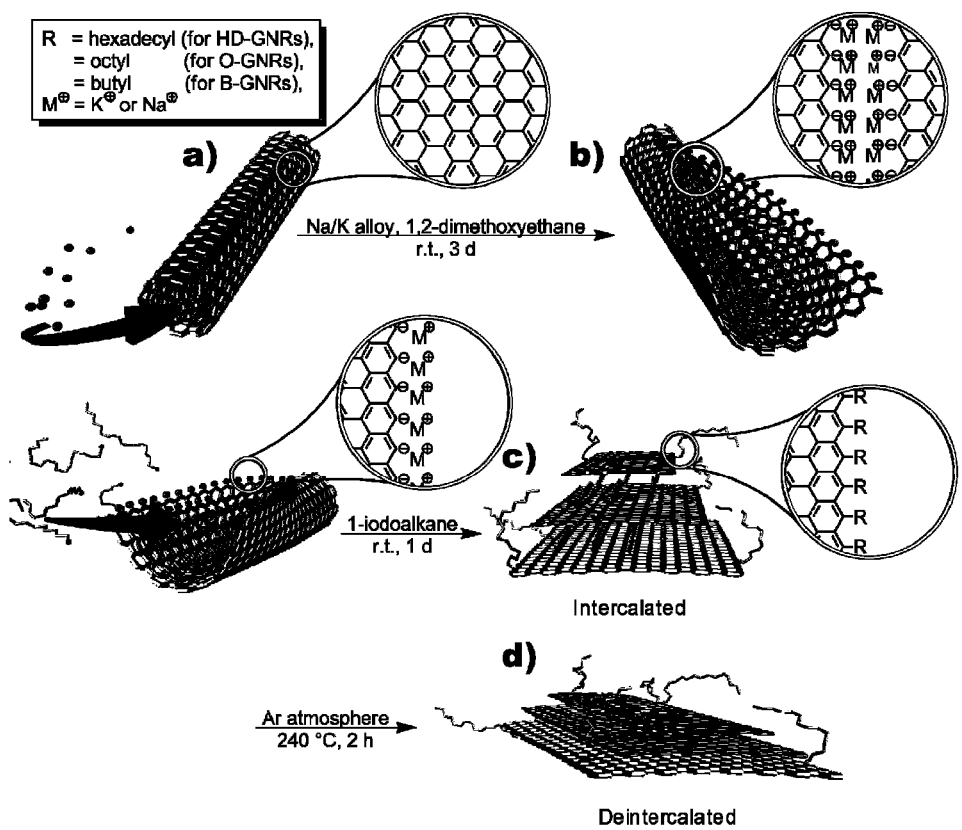
FIG. 2 provides a proposed scheme for the in-situ intercalation replacement and selective functionalization of GNRs.

The reaction scheme for the selective edge in-situ functionalization is depicted in FIG. 2. In the first step, commercially available MWNTs (Nanotech Labs, Inc. (NTL) or Mitsui & Co.) were treated with Na/K alloy in 1,2-dimethoxyethane (DME) for several days. Since K (but not Na) can be easily intercalated into graphene galleries and successfully intercalated into graphite flakes using the above conditions, Applicants envisioned that K would intercalate between the walls of the MWNTs. Applicants' previous work has shown that the intercalation of the K is accompanied by partial longitudinal cracking of the walls, as they tend to swell. Under the conditions used, it is envisioned that the edge atoms should be in the reduced carboanionic form and thus very reactive and susceptible to electrophilic attack. This reductive unzipping can be visualized as the reaction mixture changes color from a dark black or brown color to a finely dispersed green or red suspension.

The next step is the in-situ functionalization. Iodoalkanes (1-iodohexadecane, 1-iodooctane, and 1-iodobutane) are added to the reaction mixtures, presumably reacting with the active sites on the edges of the GNRs. As the reaction proceeds, the green or red color disappears. To produce proton functionalized GNRs (H-GNRs), Applicants quenched the reaction mixture with methanol. To attain the intercalated compounds with a formula as close as possible to $KC_8$ or stage 1, an excess of Na/K was used. Accordingly, it was necessary to add an excess of the iodoalkanes. This leads to side reactions, not just in the reaction solution, but also between the walls of the MWNTs. The side products include alkanes, alkenes, and dimers of alkanes.

Figure 3:
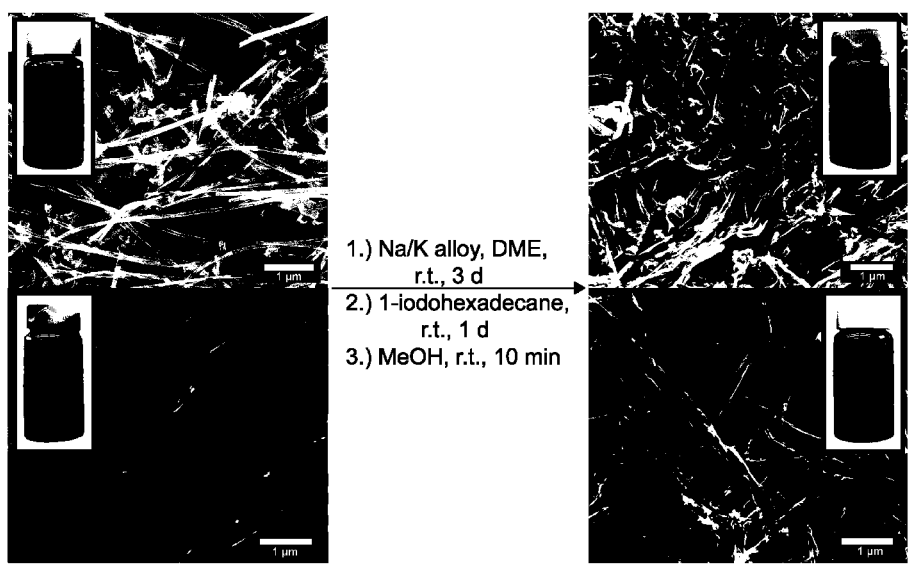
FIG. 3 provides scanning electron microscopy (SEM) images of various solubility tests. The SEM images show the splitting and functionalizing morphologies of commercially available MWNTs and the photographic differences in solubility or dispersibility (insets) between functionalized GNRs and pristine MWNTs.

As shown in FIG. 3, scanning electron micrograph (SEM) images indicate that MWNTs split to GNRs in high yields. To quench any active species that were remaining, Applicants treated the reaction mixture with methanol.

The crude materials, hexadecylated-GNRs (HD-GNRs), octylated-GNRs (O-GNRs) and butylated-GNRs (B-GNRs), were collected by filtration using 0.45 μm PTFE-membranes. The filter cakes were washed with organic solvents and water. The GNRs then underwent Soxhlet extraction to remove the majority of the physisorbed impurities.

Before analysis, all of the products were dried in vacuum (~$10^{-2}$ Ton) at 60° C. for 24 h. To the best of Applicants' knowledge, a similarly efficient in-situ one-pot method of converting MWNTs to functionalized GNR stacks has not been reported. The efficiency of the synthesis and possible scale-up makes it further attractive.

Solubility of GNRs

The solubility of pristine graphitic materials is in general known to be poor. For bulk purposes, dispersing of the material is of great importance. For solubility studies, Applicants focused on HD-GNRs. HD-GNRs exhibit an improvement in solubility and dispersability in chloroform after a short sonication using simple ultrasonic cleaner. In FIG. 3, where starting MWNTs were compared to HD-GNRs, the difference is apparent. HD-GNRs show stable dispersions in chloroform for weeks, while MWNTs cannot be dispersed using the same conditions.

Figure 4:
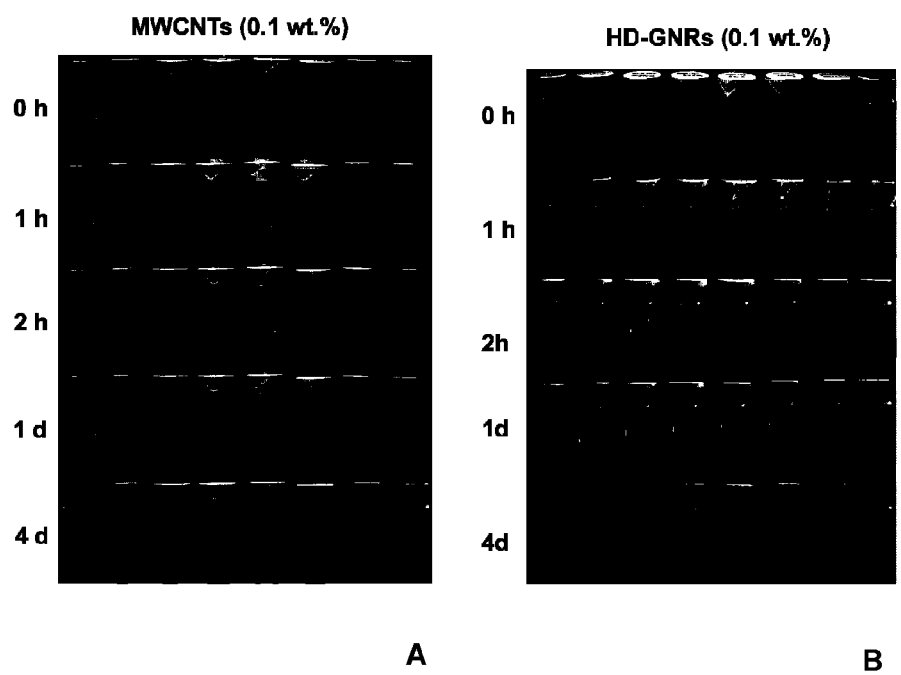
FIG. 4 shows a comparison of solubility of 0.1 wt % starting material MWNTs (FIG. 4A) and of 0.1 wt % functionalized HD-GNRs (FIG. 4B). The images show that commercial MWNTs are non-dispersible in organic solvents after short sonication using an ultrasonic cleaner. However, HD-GNRs are well dispersible in organic solvents after a short sonication.

Applicants have also performed solubility test for HD-GNRs and MWNTs at 0.1 mg/mL concentrations in different solvents. See FIG. 4. HD-GNRs are well dispersible in common organic solvents such as 2-propanol, acetone, ethyl acetate, diethyl ether, chloroform, hexane, and chlorobenzene. After 1 h, HD-GNRs settle out in hexanes and diethyl ether, while remaining dispersed in the other solvents. Four days of shelf aging resulted in sedimentation of all of the suspensions except when in chloroform and chlorobenzene, which stayed well-dispersed for weeks.

Figure 5:
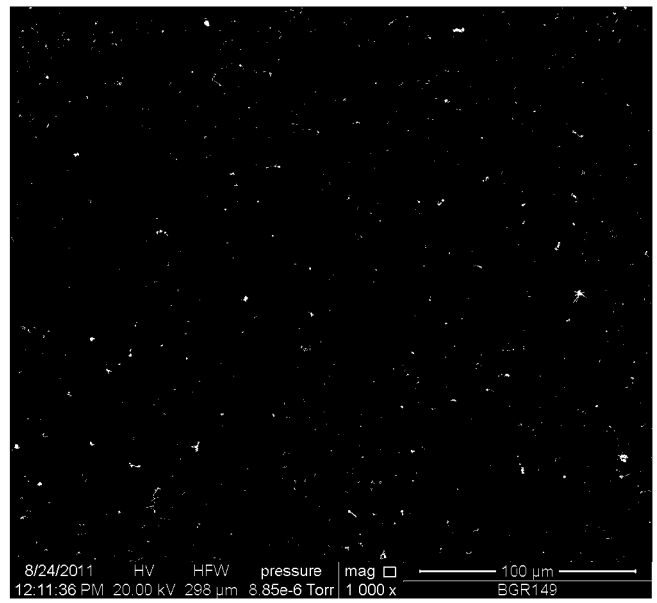
FIG. 5 provides various SEM images of HD-GNRs.
Figure 5:
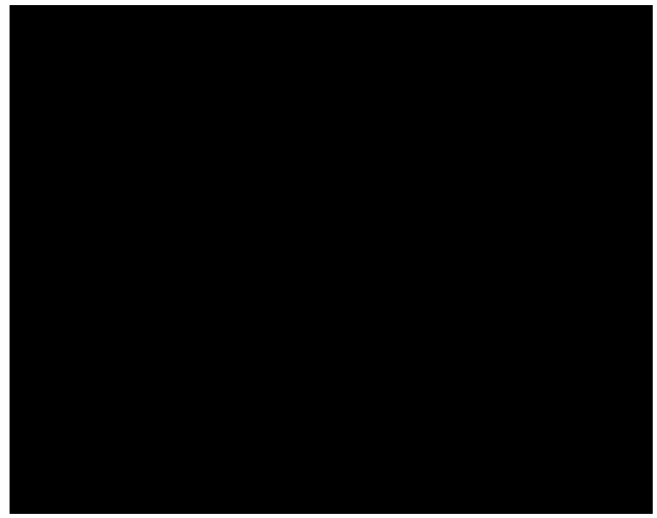

A low magnification SEM image and optical microscope image of drop cast HD-GNRs on a $SiO_2$/Si substrate show well-dispersed material. See FIG. 5. However, the starting material MWNTs showed sedimentation in all solvents tested in less than 1 h. Thus, HD-GNRs are good candidates for applications where organic dispersability is important.

Conductivity of GNRs

Figure 6:
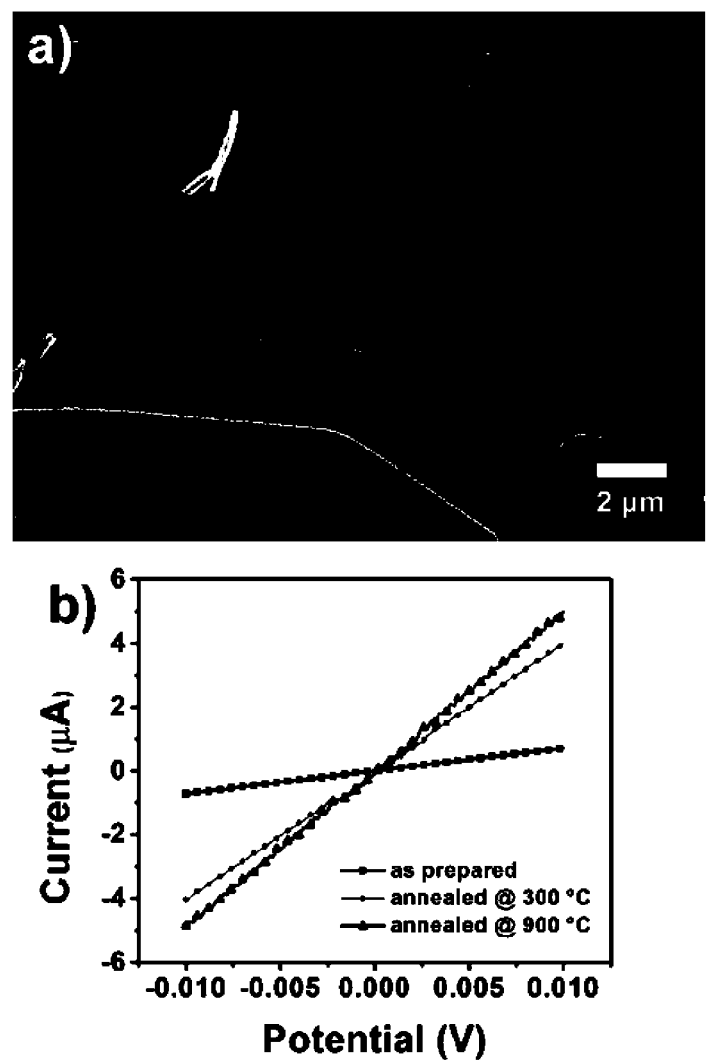
FIG. 6 shows an HD-GNR fabricated device and related conductivity measurements.

A desirable property in functionalized GNRs is the retention of conductivity, especially if they are to be used in transparent electrodes or energy-related devices, such as ultra-capacitors, Li-ion batteries and solar cells. Applicants have fabricated a single HD-GNR device by depositing 20 nm thick Pt contacts on opposite ends of GNR stacks using lithography. See FIG. 6A. The HD-GNR stack used in the device was 7.9 µm long, ~300 nm wide (FIG. 7) and ~30 nm thick. The thickness was estimated from the atomic force microscopy (AFM) image. See FIG. 8. As-prepared, the single ribbon device exhibited a conductivity of 600 S/cm, as measured by Equation 1.

$$\text{Conductivity} (S/cm) = \frac{L \text{ (cm)}}{R(\Omega) * t(\mu m) * W(\text{cm}) * 0.0001} \quad \text{(Eq. 1)}$$

The data used to calculate conductivity are summarized in Table 1.

TABLE 1

The data used for calculating conductivity with Eq. 1.

| Resistance R (Ω) | Resistivity R (Ωcm) | Conductivity s (S/cm) | GNR Thickness t (µm) | GNR Width W (cm) | GNR Length L (cm) | Temperature of annealing ° C. |
|---|---|---|---|---|---|---|
| 2060 | 0.0002347 | 4261.06 | 0.03 | 0.00003 | 0.00079 | 900 |
| 2480 | 0.0002825 | 3539.42 | 0.03 | 0.00003 | 0.00079 | 300 |
| 14600 | 0.0016633 | 601.22 | 0.03 | 0.00003 | 0.00079 | 25 |

The conductivity increased almost six times to 3540 S/cm when the device was annealed at 300° C. Without being bound by theory, it is envisioned that there are at least two reasons for such a difference in conductivity between the as-prepared sample and the sample annealed at 300° C. The conductivity could be partially increased due to improved contact between the electrodes and the GNR stack. However, previous work on graphene materials with Pt-contacts shows that the good wetting of the carbon with Pt leads to a low-barrier contact. Thus, the main contribution is likely due to deintercalation of hydrocarbons (but not necessarily defunctionalization) from the graphene galleries.

The intercalated graphene galleries are electrically isolated from each other, as alkanes are known insulators. Deintercalation reinstates the interaction between the graphene layers. A control experiment where HD-GNRs were heated at 300° C. for 2 h showed that their solubility in chloroform after annealing was comparable to the as-prepared HD-GNRs. The latter result speaks in favor of the HD functional groups staying intact at temperatures up to 300° C. When the device was further heated to 900° C., a temperature at which the HD functional groups are expected to have cleaved from the GNRs, the conductivity increased to 4260 S/cm. This small increase could indicate that edge functionalization does not substantially disturb the conductivity of the graphene basal planes. The conductivities of the functionalized HD-GNRs are comparable to previous literature reports on pristine materials such as graphite (200-8300 S/cm), CNTs (1000-100000 S/cm) and GNRs (~800 S/cm) and thus interesting for further study.

Bulk conductivities of as-prepared samples were also measured using four-point probe measurement on pressed pellet, in accordance with equation 2.

$$\sigma(S cm^{-1}) = \frac{ln2 \times I(mA)}{\pi \times U(mV) \times \text{pellet thickness (cm)}} \quad \text{(Eq. 2)}$$

Figure 9:
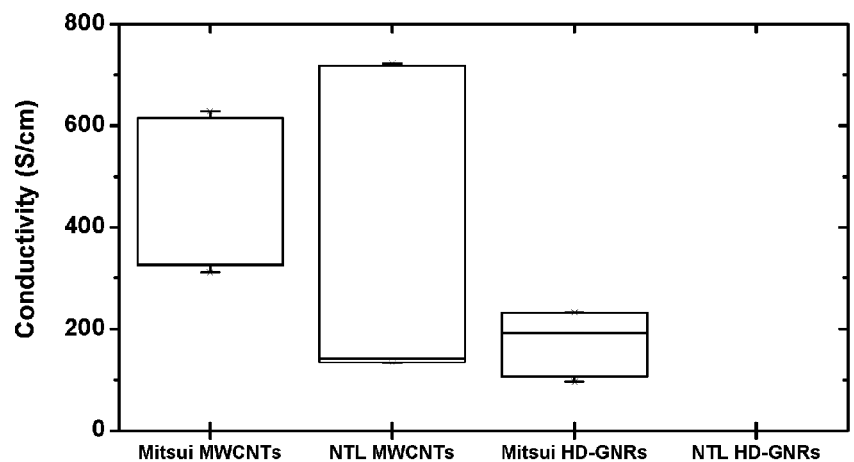
FIG. 9 provides various conductivity measurements for MWNTs and HD-GNRs.
Figure 9:
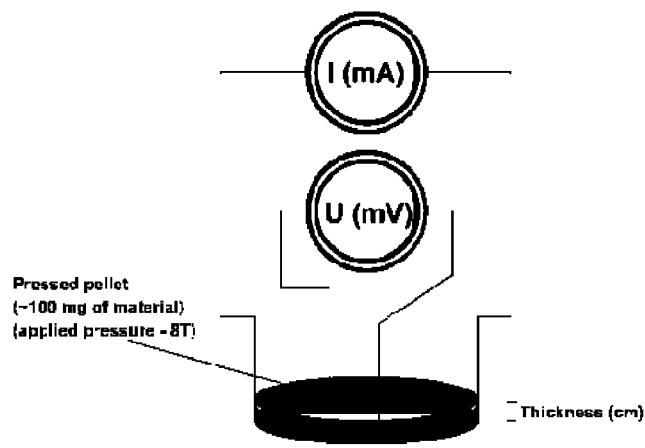

Similarly, relatively high conductivity ranging from 145 to 175 S/cm was observed, which is only 2.5 times smaller than conductivities of the starting material MWNTs. See FIG. 9.

Evolved Gas Analysis (EGA) of GNRs

Figure 7:
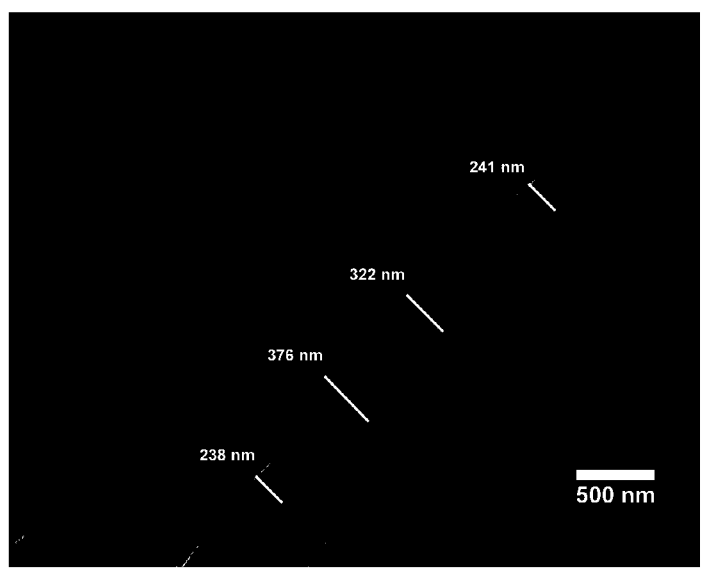
FIG. 7 is an SEM image showing width of a single HD-GNR used in a device for conductivity measurements.
Figure 8:
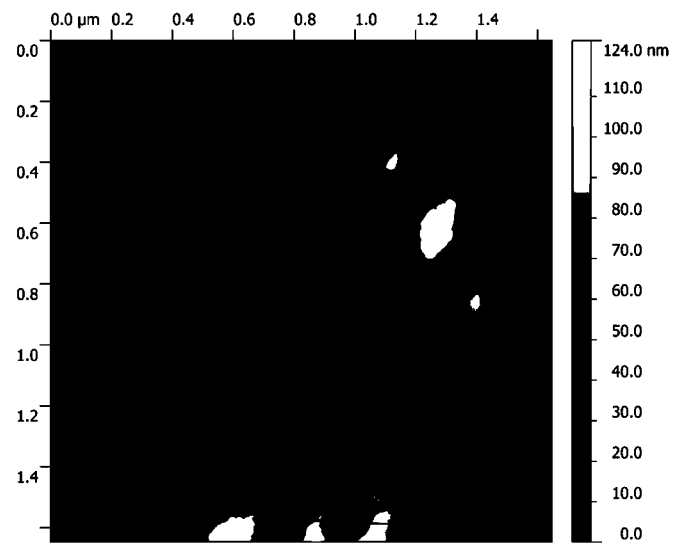
FIG. 8 provides an atomic force microscopy (AFM) image (FIG. 8A) and profile plot (FIG. 8B) of a single HD-GNR used in a device for conductivity measurements. AFM images were obtained with a Digital Instruments nanoscope Ma, operating in tapping mode, using Si tips n-doped with 1-10 Ωcm phosphorus (Veeco, MPP-11100-140).
Figure 8:
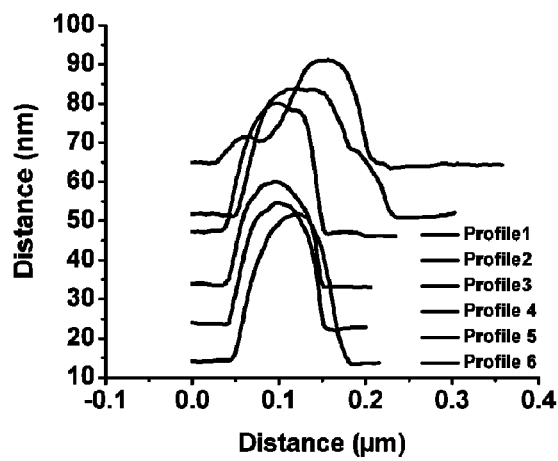
Figure 10:
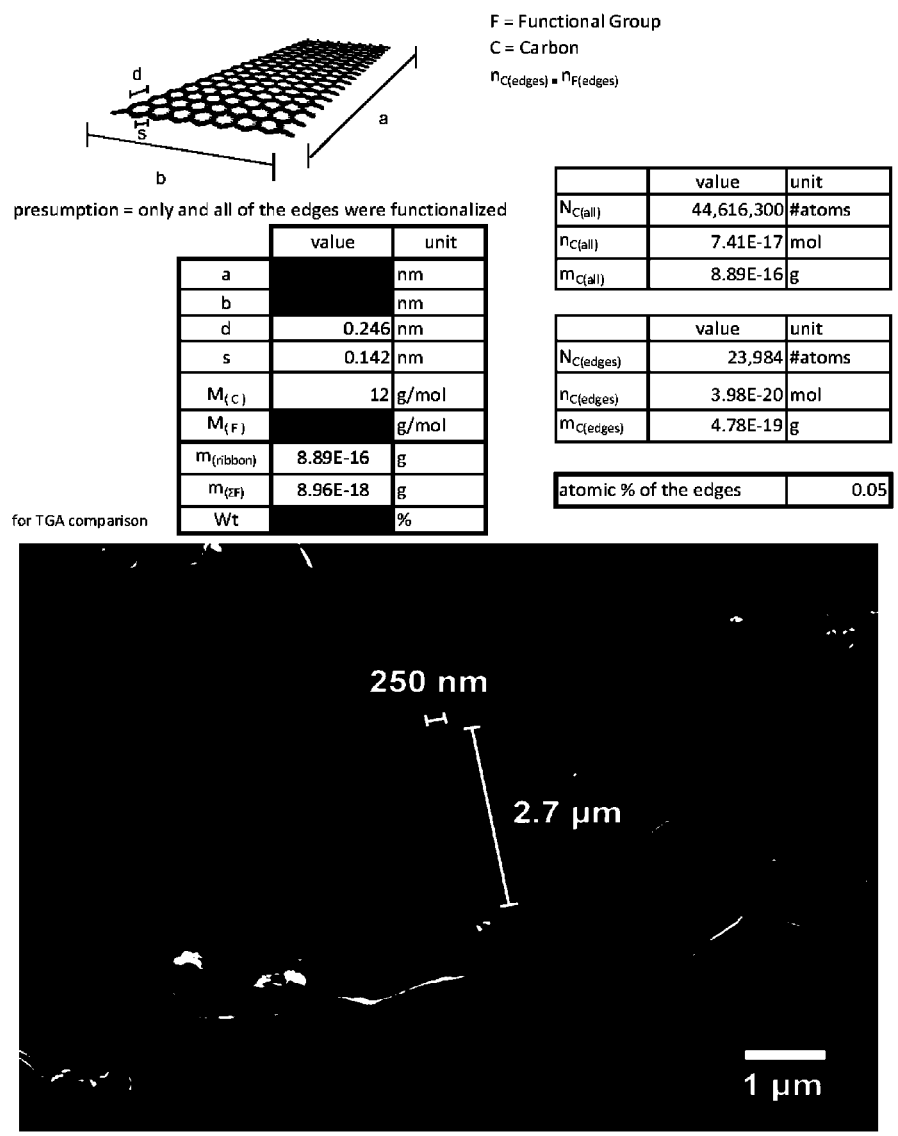
FIG. 10 provides calculation of the hypothetical degree of edge functionalization with HD groups (top). The length and width were estimated from the SEM image (bottom). The presumption was made that only the edge carbons are functionalized.

Confirming edge functionalization versus intercalation remains challenging, particularly due to the expected low degree of edge carbons to non-edge carbons. The average GNRs stack with 250 nm width×2.7 µm length dimensions (estimated from the SEM image, as shown in FIG. 7) should have only 0.05 atomic % of edge carbons in GNRs (FIG. 10). If all of the edge carbons are functionalized, then the functional groups would contribute 1 wt % of the total weight to the HD-GNRs; 0.5 wt % if considering O-GNRs, and 0.25 wt % if considering B-GNRs.

Since the expected degree of functionalization is low, Applicants have used thermogravimetric analysis (TGA) coupled with a quadrupole mass spectrometer (QMS) to detect thermalized products. The sensitivity of QMS should give some insight into the quantitative nature of the alkylated graphene nanoribbons (A-GNRs). TGA of HD-GNRs shows a total weight loss of 37% in the range between 40° C. and 900° C., which is far above the expected value of 1% (FIG. 11A).

Figure 11:
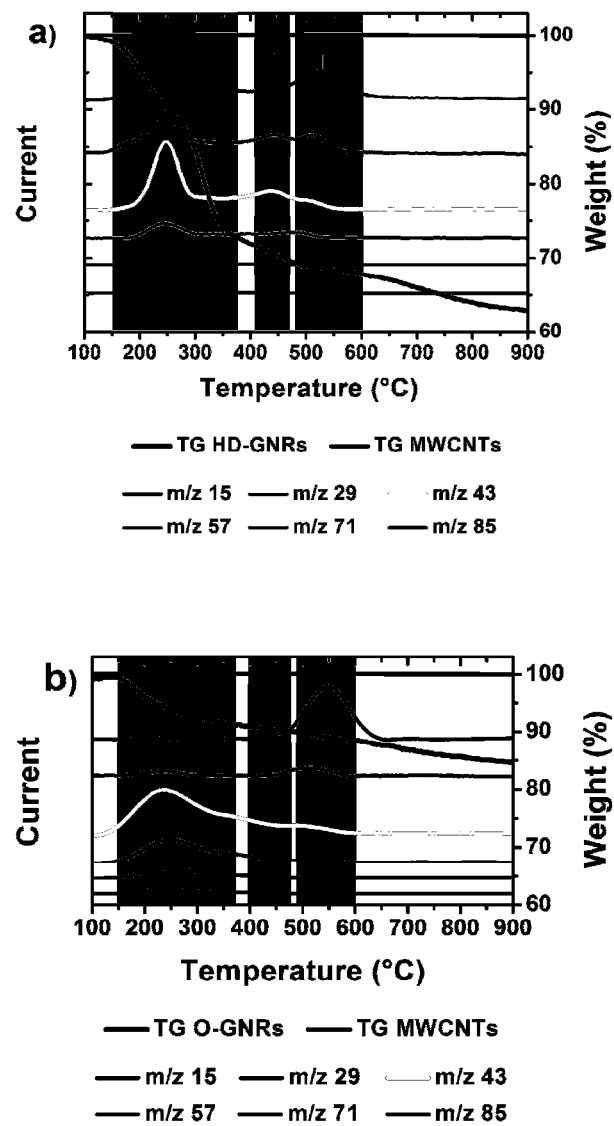
FIG. 11 provides data relating to the evolved gas analysis (EGA) of various GNRs. Different colors represent fragments with m/z that correspond to alkane fragments. Black and gold curves represent the thermographic analysis (TGA) profile of functionalized GNRs and pristine MWNTs, respectively. Gray rectangles represent Region I, Region II and Region III, respectively. TGA-MS of HD-GNRs (FIG. 11A), Octylated-GNRs (O-GNRs) (FIG. 11B) and butylated-GNRs (B-GNRs) (FIG. 11C) are shown.
Figure 11:
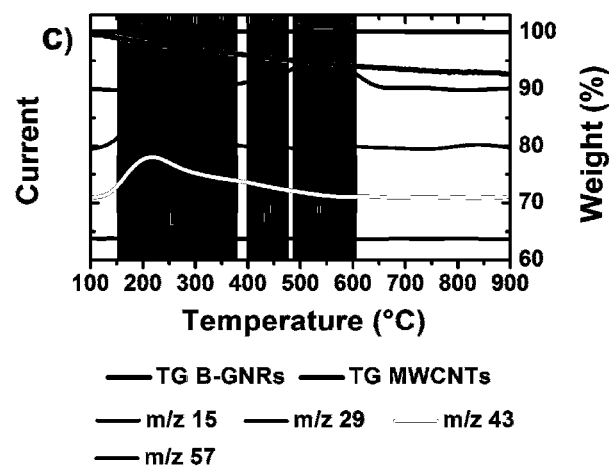

The reference compound, hexadecane, has a specific fragmentation pattern, with high abundance fragments with decreasing intensities at m/z=57, 43, 71, 85, 29, and 99. Similar patterns are expected for octane m/z 43, 57, 29, 85, 71, and for butane m/z 43, 29, 15, 57. These fragments were also found in the evolved gases during the TGA, indicating that alkyl groups are present in the A-GNRs samples (FIG. 11).

However, there are three distinct temperature ranges during which the alkyl groups are present in the off-gas from HD-GNR thermolysis products (FIG. 11A). The first is the range between 154° C. and 374° C. (Region I), where the weight loss is 26%. The second range is between 400° C. and 474° C. with a weight loss of 2% (Region II). The third range between 480° C. and 612° C. had a 2% weight loss (Region III).

As explained herein, Region I is assigned to deintercalation of alkanes. Regions II and III were assigned to covalently bound alkyl groups, most likely hexadecyl. The temperature interval for Region II corresponds with previous reports on covalently attached organic moieties on different carbon substrates. The mass spectrometer detection limit is up to 100 atomic mass units. Thus, the molecular ion corresponding to the hexadecyl moiety could not be detected. Fragments m/z 29, 15, 43, 57, 85, and 71 that are present in Region II are indications that fragmentation due to thermal cleavage of the hexadecyl group is most likely occurring. The major fragments present in Region III are the methyl and ethyl groups (m/z 15, 29), which could be the remainder of the hexadecyl group bound directly to the graphene substrate. Similar results were obtained for O-GNRs and B-GNRs (FIGS. 11A and 11C), where Applicants observed 7 wt % loss between 139° C. and 293° C., and 4 wt % loss between 121° C. and 247° C. for Region I, respectively. Region II between 448° C. and 526° C. for O-GNRs shows a 1 wt % loss, while Region III between 526° C. and 628° C. had a 1.3 wt % loss. B-GNRs show 1.3 wt % loss for Region II between 328° C. and 453° C., and 1.7 wt % for Region III between 453° C. and 636° C. According to this data and the assumption that Regions II and III correspond to the same functional groups but have different fragmentation temperatures, the degree of functionalization is 4.6% for HD-GNRs, 2.3% for O-GNRs and 3% for B-GNRs.

Figure 12:
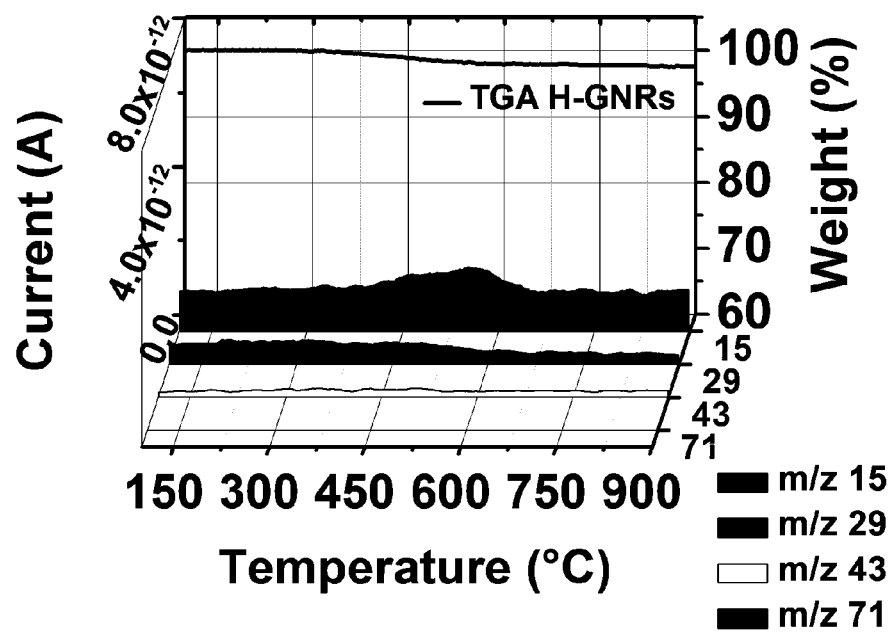
FIG. 12 shows the EGA for hydrogen terminated GNRs (H-GNRs). The colors represent fragments with m/z 15 (red), 29 (orange), 43 (yellow) and 71 (cyan) that correspond to alkane fragments. The black curve represents the TGA profile of the H-GNRs.

To exclude the reaction between solvent and active GNRs, EGA of methanol quenched, thus hydrogen terminated GNRs (H-GNRs), was also done. TGA-MS analysis confirmed the absence of all fragments except m/z 15, the methyl fragment between 400° C. and 600° C. (FIG. 12). The methyl fragment could be the result of rearrangements with successive cleavage on defects and edges where carbons are expected to be hydrogen-terminated or from trace methanol.

X-Ray Powder Diffraction (XRD) Analysis of HD-GNRs

For direct evidence of deintercalation in Region I, HD-GNRs thermally treated at temperatures of 240° C., 530° C. and 900° C. were prepared. XRD diffractograms of the samples were then recorded and analyzed (FIG. 12A). The total weight loss for the sample heated at 240° C. for 2 h was 26%, which corresponds to the weight loss in Region I in FIG. 13A. For the sample heated at 530° C. for 2 h, the weight loss was 32%, and for the sample heated at 900° C. for 20 min, the weight loss was 39%. The TGA plots of the thermally treated HD-GNRs samples are shown in FIG. 14.

The XRD diffractogram for the as-prepared sample contains well-pronounced diffraction lines at 12.0° and 24.2° 2θ angle, which correspond to the (001) and (002) signals of a stage 1 intercalation compound, respectively. The calculated c-axis repeat distance ($I_c$) is 0.738 nm, which is the typical spacing ($d_s$) between the two carbon layers sandwiching the layer of intercalant. As one can see from FIG. 13A, both the 12.0° and 24.2° signals disappear after heating at 240° C. The new diffraction line at 26.2° 2θ angle corresponding to the (002) signal of graphite appears instead.

Figure 14:
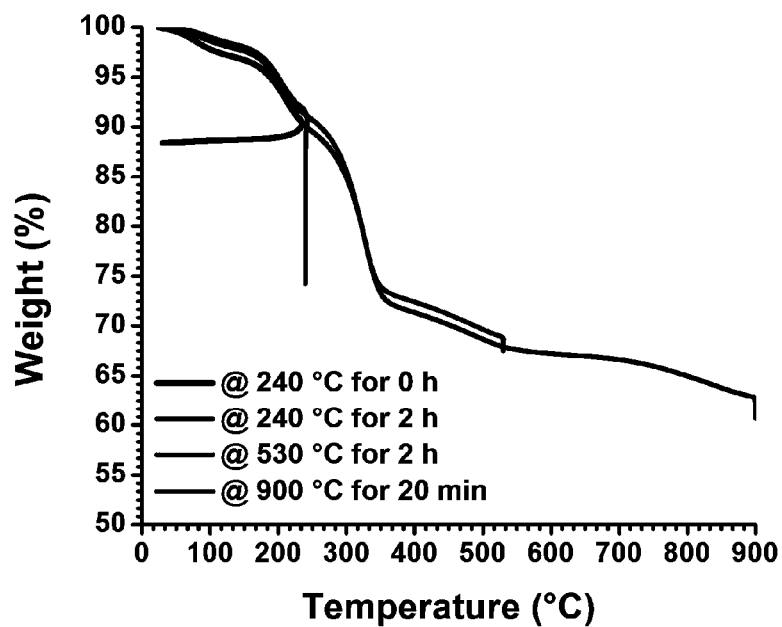
FIG. 14 provides TGA plots of thermally treated HD-GNRs. The curves represent the weight loss of HD-GNRs thermally treated at different temperatures. Blue curve: the HD-GNRs were heated to 240° C. and then cooled to room temperature without holding at 240° C.; the product was partially deintercalated. Green curve: the HD-GNRs were heated at 240° C. for 2 hours; the product was fully deintercalated. Orange curve: the HD-GNRs were heated at 530° C. for 2 hours; the product was fully deintercalated and partially defunctionalized. Red curve: the HD-GNRs were heated at 900° C. for 20 minutes; the product was fully deintercalated and completely defunctionalized.
Figure 15:
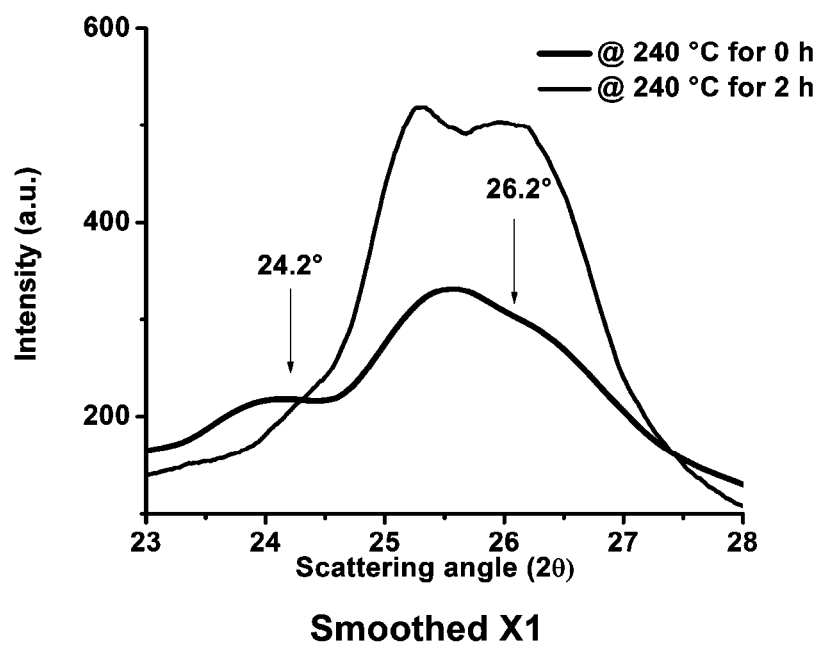
FIG. 15 provides powder diffraction patterns of samples heated up to 240° C. for less than a minute, and samples heated at 240° C. for 2 hours.

The sample heated to 240° C. and then cooled to room temperature can be considered an intermediate state between the fully intercalated as-prepared sample and the one heated for 2 h at 240° C. The weight loss during heating to 240° C. was ~12% (FIG. 14). The sample that was heated and then cooled contains both the 24.2° signal and the 26.2° signal in a ratio of ~1:2 (FIG. 15). Interestingly, no intermediate stage compound was detected in the sample.

Such results are unexpected for graphite intercalation compounds (GICs), where graphite gradually intercalates and then gradually deintercalates, sequentially going through all the stage numbers. Instead Applicants detected only the two states, the stage 1 GIC, and the non-intercalated graphitic GNRs. Without being bound by theory, Applicants suggest that the mixed stage comes from different GNRs. Individual GNRs likely deintercalate quickly and completely. Therefore, it is envisioned that the observed "mixed stage" is a mixture of completely intercalated and completely deintercalated individual GNR stacks.

Figure 13:
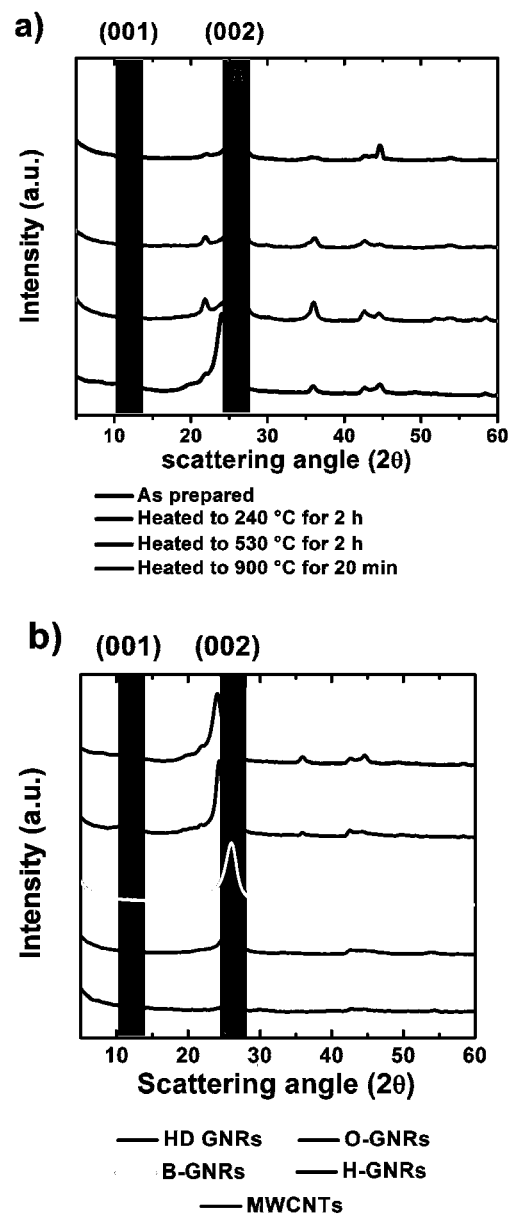
FIG. 13 shows powder diffraction patterns for various GNRs and MWNTs.

Samples heated at temperatures of 530° C. and 900° C. are completely deintercalated and give diffractograms identical to H-GNRs or the starting material MWNTs (FIG. 13B). Since weight losses of 7% and 4% were also observed for O-GNRs and B-GNRs in Region I, XRD diffractograms were also recorded for as-prepared samples. However, O-GNRs show similar intercalation compounds as HD-GNRs, with L spacing between graphene layers of 0.731 nm. Interestingly, B-GNRs do not show any intercalation (FIG. 13B), since the diffractograms are identical to H-GNRs or MWNTs.

Without being bound by theory, it is envisioned that the reason for the aforementioned observations might be in the size of the intercalant. In the case of HD-GNRs, it is expected to be at least 16 or 32 carbon chains (the latter is the dimer product). For O-GNRs, the spacing would be about half of 0.731 nm. For B-GNRs, the spacing would be about one-fourth of 0.731 nm. Hexadecane and octane are higher boiling point liquids, while dotriacontane is a solid. On the other hand, butane is a gas which is likely too volatile and mobile to form a stable GIC. For HD-GNRs, the proposed major intercalant is dotriacontane, but others cannot be excluded.

The synthesis of HD-GNRs, as discussed earlier, leads to side products that are also potential intercalants. Two control experiments produced evidence that dotriacontane is indeed the main component. In the first control experiment, 1-iodohexadecane was added into the dispersion of Na/K in DME. Gas chromatography-mass spectrometry (GC-MS) showed the presence of 1-hexadecene and hexadecane as minor components (21% and 19%, respectively) and dotriacontane as the major component (60%) of the reaction mixture.

Figure 16:
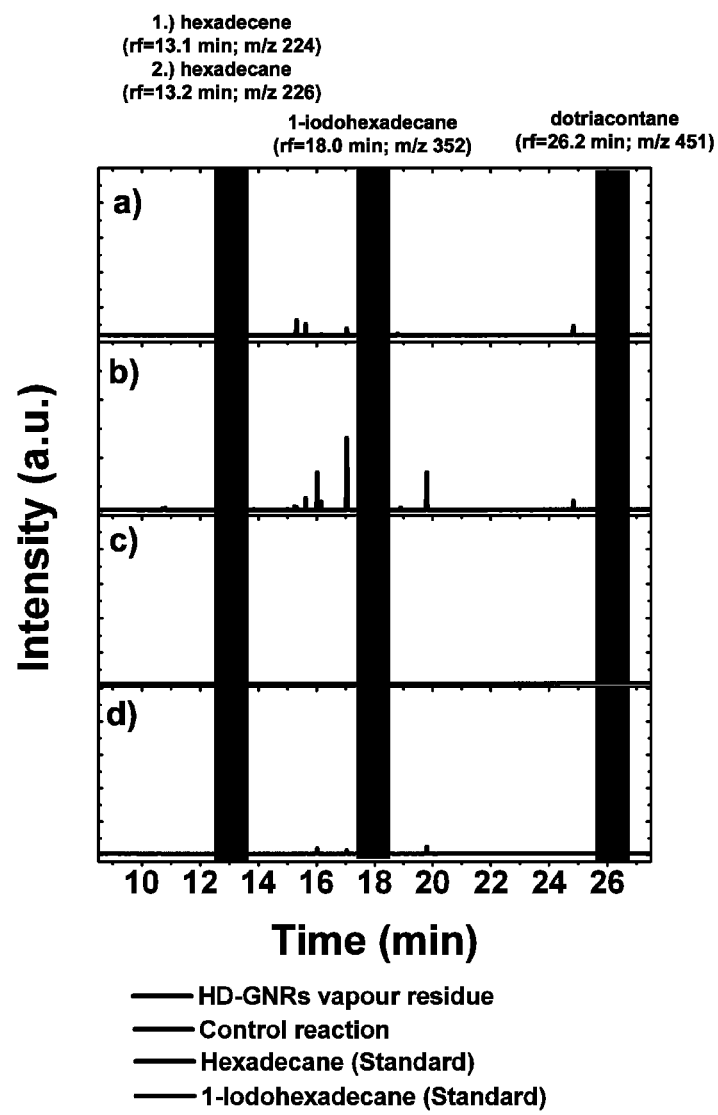
FIG. 16 provides gas chromatography-mass spectrometry (GC-MS) of control experiments for qualitative and quantitative intercalant determination.

Another experiment with as-prepared HD-GNRs was done. HD-GNRs were heated at 150° C. in vacuum. A cold finger cooled to 0° C. was connected to the system to capture products that were released. Analysis of the collected vapors using GC-MS again showed dotriacontane as the major component (45%). Other components detected were 1-hexadecene (6%), hexadecane (35%) and starting material 1-iodohexadecane (13%, for the GC-MS analysis, as shown in FIG. 16).

Solid-state $^{13}C$ nuclear magnetic resonance spectroscopy (SS NMR) of HD-GNRs To further investigate the nature of the intercalant, two types of magic angle spinning (MAS) NMR experiments were performed. The relatively high conductivity of HD-GNRs caused severe probe tuning problems, which initially prevented useful $^1$H—$^{13}$C cross polarization (CP) and direct $^{13}$C pulse spectra from being obtained. However, dispersing the sample in silica (an approach previously used to obtain a $^{13}$C spectrum of graphite[30]) enabled the $^{13}$C and $^1$H channels to be properly tuned on a sample of 10 wt % HD-GNRs and 90 wt % silica.

In the CP spectrum of the unheated material (FIG. 17, red spectrum), two broad, overlapping bands are evident. The band centered at about 90 ppm is thought to be from several types of carbons: graphene sheet sp$^2$ C—H carbons, graphene sheet sp$^2$ carbons that are either on or near the edge of the sheet or near a covalently bound hexadecyl group or intercalated alkane and thus are capable of being cross polarized, and from the downfield tail of the signal from the methylene carbons in covalently bound hexadecyl groups and in intercalated side products (e.g., hexadecane, 1-hexadecene, and dotriacontane). The band centered at about 90 ppm is unusually broad and shielded, as is the signal from the carbons detected in a direct $^{13}$C pulse spectrum of graphite dispersed in silica. The breadth of the band centered at about 90 ppm can be at least partially attributed to the inability of MAS to completely remove the anisotropy of the magnetic susceptibility in the graphene sheets, while the shielding can be attributed to the diamagnetic shift in the $\delta_{33}$ component of the shielding tensor of the numerous graphene carbons in a very large condensed aromatic ring system. This broadening and shielding is reminiscent of what is observed as graphite oxide is steadily reduced and becomes increasingly like graphite.

Figure 17:
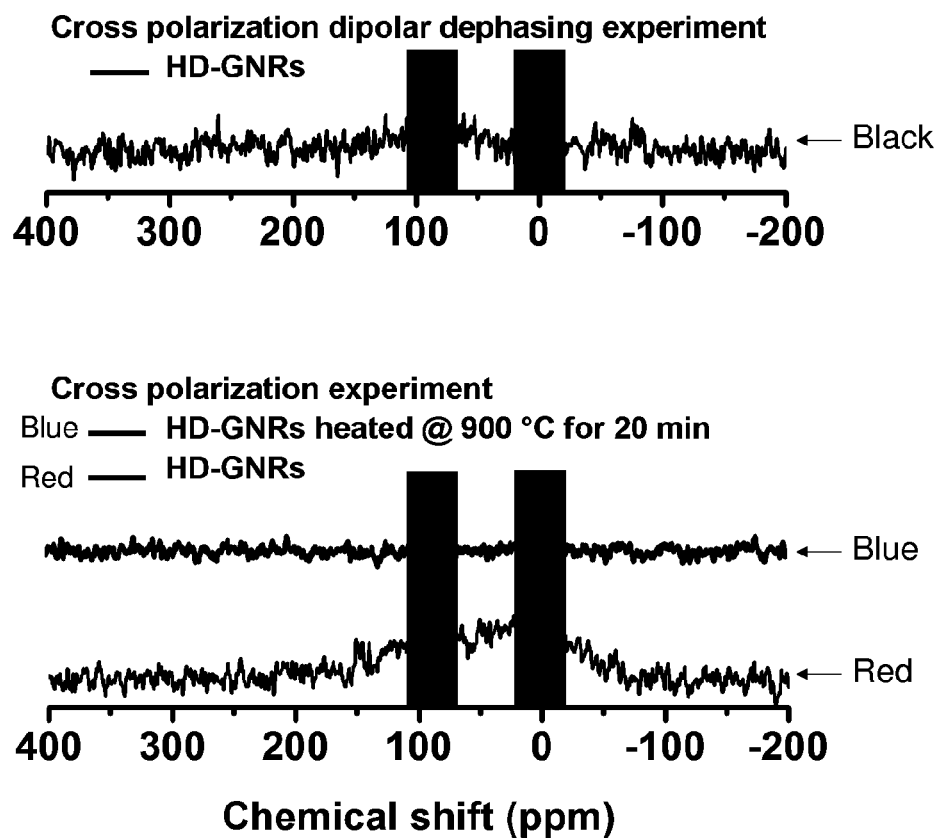
FIG. 17 is a solid-state nuclear magnetic resonance (SS NMR) images. Cross polarization experiment of functionalized and intercalated HD-GNRs (red curve) and defunctionalized and deintercalated HD-GNRs after heating at 900° C. for 20 min (blue curve) are shown. Cross polarization dipolar dephasing experiment of functionalized and intercalated HD-GNRs (black curve) is also shown.

The band centered at about 0 ppm in FIG. 17 is thought to be from the methylene carbons indicated above and from the upfield tail of the signal from graphene sheet sp$^2$ carbons. The band centered at about 0 ppm is also unusually shielded, as would be expected if the covalently bound hexadecyl groups or intercalated alkanes are sandwiched between the graphene sheets and thus are subjected to a large diamagnetic susceptibility resulting from delocalized electrons (a π-electron ring current) in the graphene sheets. Indeed, a less dramatic shielding effect but much better resolution are observed with anthracite bearing dodecyl groups on the edges.

In contrast, the central methylene carbons in methylene chains constrained to be above an aromatic ring in molecules such as [12]-paracyclophane and various 1,n-dioxa[n](2,7) pyreneophane experience only a very small ring current shielding effect. The much weaker signal from the methyl carbons in the HD-GNRs is not recognizable.

The 50-µs dephasing period in the dipolar dephasing experiment on the unheated material (FIG. 17, black spectrum) strongly attenuates the band centered at about 90 ppm and completely eliminates the band centered at about 0 ppm. Since this dephasing period is designed to eliminate CH and CH$_2$ signals with minimal attenuation of quaternary carbon signals, the less shielded band in the basic (red) CP spectrum has significant contributions from graphene sheet sp$^2$ C—H carbons and the downfield tail of the signal from the various methylene carbons, while the more shielded band in the basic CP spectrum is consistent with the various methylene carbons and the upfield tail of the signal from graphene sheet sp$^2$ C—H carbons. The relatively immobile nature of the covalently bound hexadecyl groups and intercalated alkanes results in a correspondingly strong $^1$H—$^{13}$C dipole-dipole interaction that both makes it possible for these methylene groups to cross polarize (red spectrum) and then to have the signal rapidly decay (black spectrum). The very weak signal centered at about 90 ppm in the dephasing experiment may result from the attenuated signal from graphene sheet sp$^2$ carbons that poorly cross polarized.

The CP spectrum of the heated material (FIG. 17, blue spectrum) shows no signal above the noise. As seen from the conductivity, TGA, and XRD results, defunctionalization and deintercalation at this temperature is complete. With no covalently bound hexadecyl groups or intercalated alkanes remaining, no NMR signal is detected. The importance of these hexadecyl groups and alkanes for generating the signals in the spectrum of the unheated material (red spectrum) is evident.

Raman Spectroscopy of HD-GNRs

Figure 18:
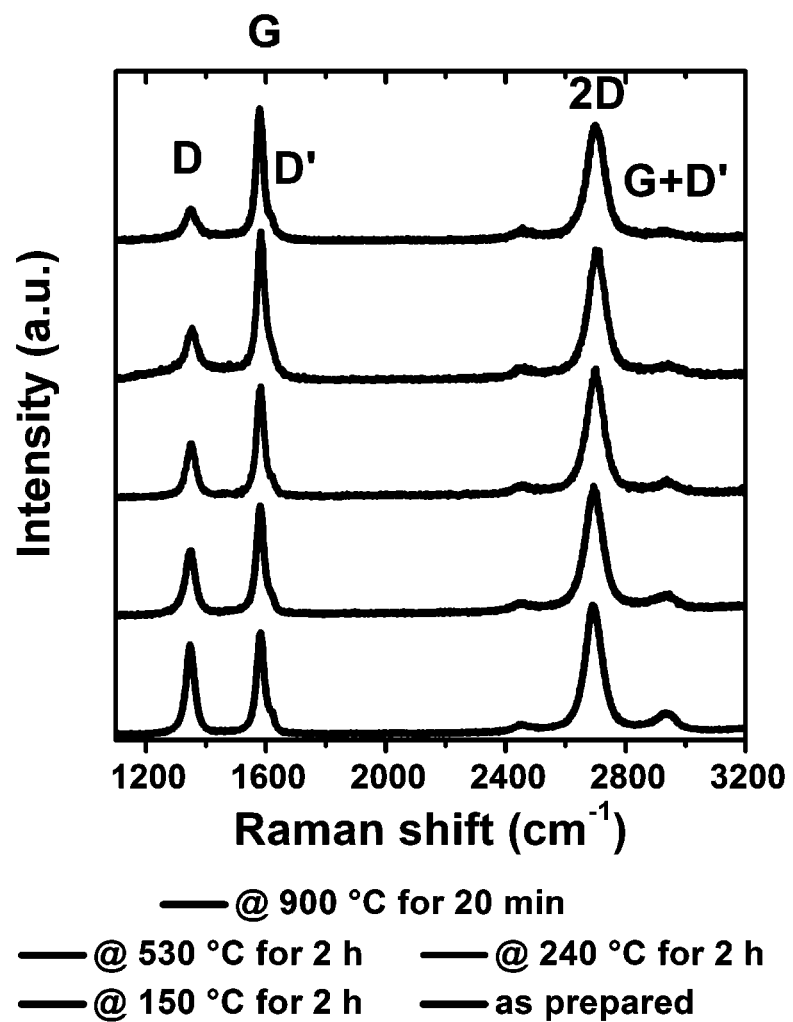
FIG. 18 shows Raman spectra that compare thermally treated HD-GNRs with as-prepared GNR samples.

The Raman spectrum of the as-prepared sample is significantly enhanced compared to the heated samples (FIG. 18). This is an additional argument in support of formation of the intercalation compound. It is known that when several species are intercalated into graphite, or simply physisorbed on the graphene surface, the Raman spectra are enhanced. No blue-shift of the G-peak is detected, however. This suggests that the intercalant in HD-GNRs is neutral toward carbon and does not charge the carbon layers. The spectrum of the as-prepared sample contains a D-peak at ~1360 cm$^{-1}$ of very high intensity and the G+D' peak at ~2950 cm$^{-1}$. This suggests that significant disorder in the system was induced by splitting and intercalation. Such results are unexpected because for most of the known GIC compounds, intercalation does not cause appearance of the D-band. The D-band gradually decreases with heating and is finally of the same magnitude as non-intercalated split GNRs. The D/G ratio can be considered a measure of disorder. The fact that it decreases suggests that disorder induced by the intercalant decreases when the intercalant is removed. The 2D peak in both the parent MWNTs and GNRs is single-Lorentzian, suggesting no AB stacking. This is quite natural, since the walls in MWNT have different chiralities. They retain their structure after splitting. Hence, the layers in the GNR have some degree of single-layer character.

Figure 19:
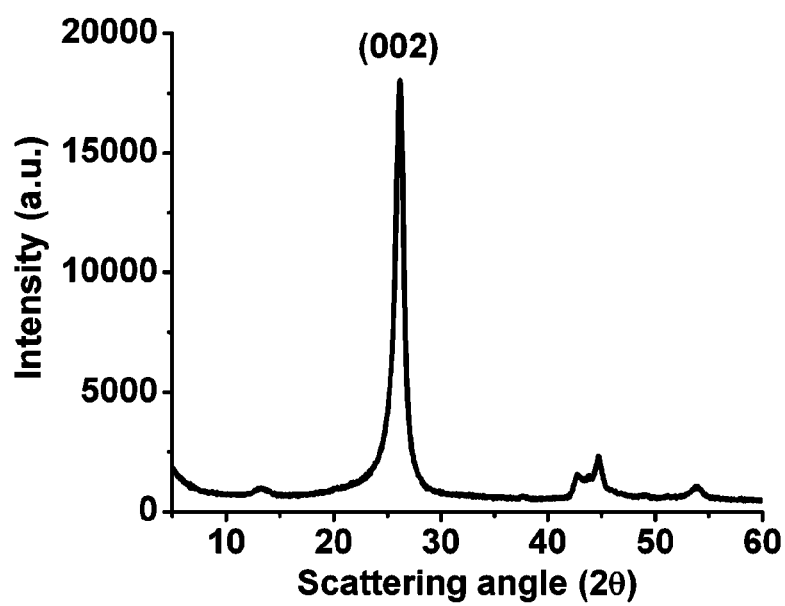
FIG. 19 shows x-ray diffraction (XRD) patterns of the product of the control reaction with hexadecane that displays a well-pronounced diffraction line at 26.2° 2θ angle. This diffraction line corresponds to the (002) signal and is similar to the diffractogram of H-GNRs or MWNTs, which means that intercalation does not occur when hexadecane is used instead of 1-iodohexadecane.
Figure 20:
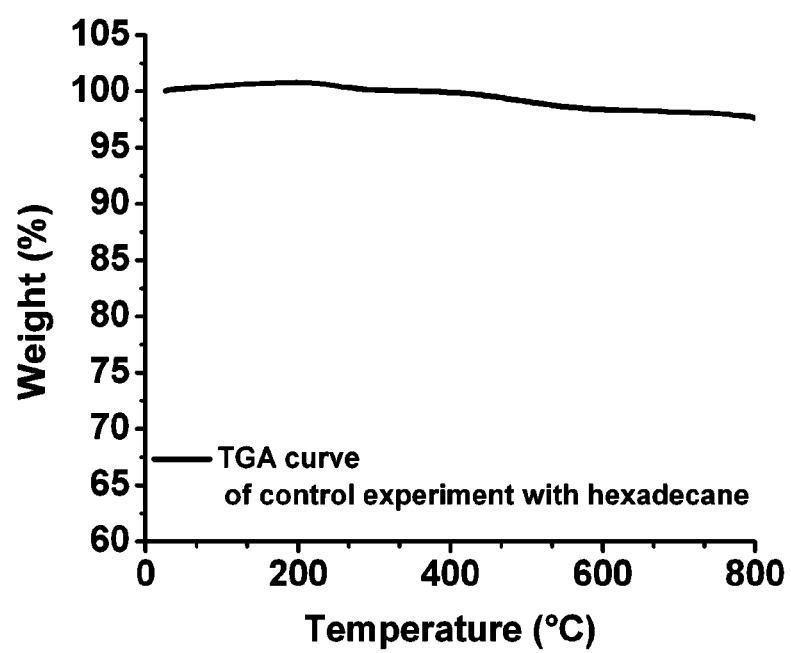
FIG. 20 is a TGA curve of the product of a control reaction with hexadecane.

Without being bound by theory, Applicants hypothesize that intercalation is possible only when the reaction of intercalated K and 1-iodoalkane occurs between graphene sheets. The by-product KI is forced out, while newly formed alkanes and alkenes (as well as covalently bound alkyl groups) take their places between sheets. For this process, the term "replacement-driven intercalation" is introduced. To partially confirm the latter hypothesis, Applicants performed a control experiment, where instead of 1-iodohexadecane, hexadecane was used. Under the same reaction conditions, no intercalation was observed, which was confirmed by XRD (FIG. 19), where the (002) signal was observed at 26.2° 2θ angle, which corresponds to non-intercalated material. The results were also confirmed by TGA (FIG. 20), where Applicants observed a weight loss of ~2% in the region between room temperature and 800° C.

SUMMARY

In this Example, a high yielding conversion of commercially available MWNTs to in-situ functionalized GNRs stacks was achieved by a reductive method. GNRs bearing long alkyl chains are well-dispersible in organic solvents such as alcohols, ketones, ethers and alkanes. Particularly stable dispersions are produced in chloroform or chlorobenzene. HD-GNRs exhibit relatively high GNR conductivity as well as bulk material conductivity. The conductivity of ~3540 S/cm of single deintercalated HD-GNR was achieved through minimal interruption of the conjugated π-system of the basal plane. Therefore, Applicants propose that functionalization occurs preferably on the edges of graphene. The concept of edge functionalization was partially supported by EGA, enhanced solubility and relatively high conductivity of single and bulk functionalized material. Replacement of intercalated addends was observed and thoroughly investigated for the HD-GNRs and O-GNRs. TGA-MS showed deintercalation of alkanes and alkenes at temperatures between 140° C. and 300° C. XRD revealed stage 1 intercalation compound for the as-prepared samples. Interestingly, no intermediate stage compounds were detected. GC-MS showed dotriacontane as major intercalant compound in HD-GNRs. Further, solid-state $^{13}$C nuclear magnetic resonance spectra of HD-GNRs were consistent with the presence of methylene carbons in covalently bound hexadecyl groups and intercalated alkanes, as the signal attributed to the methylene carbons is unusually shielded and disappears after the sample is deintercalated and defunctionalized by heating. Similarly, Raman spectroscopy for the as-prepared sample indicated the intercalation compound. XRD and Raman spectroscopy revealed that thermal treatment of intercalated HD-GNRs up to ~300° C. leads to full deintercalation. However, covalently bound functional groups are stable at that temperature and still provide enhanced solubility, as the deintercalated HD-GNRs are still soluble in organic solvents.

Materials and Methods

Reactions were performed in dried glassware under an $N_2$ atmosphere unless stated otherwise. Reagent grade 1,2-dimethoxyethane was degassed with Ar, refluxed over sodium in an $N_2$ atmosphere and freshly distilled. Other solvents were used without further distillation. Mitsui MWNTs were received from Mitsui & Co. (lot no. 05072001K28). NTL-M grade MWNTs were obtained from Nanotech Labs, Inc. (5T10M10). All other commercially available reagents were used as received. Liquid Na/K alloy was prepared in a vial inside of a $N_2$ glove box by pressing together freshly cut K (1 molar equivalent) and Na (0.22 molar equivalents) chunks using tweezers to facilitate the melting process. Amounts of liquid Na/K alloy indicated are by volume.

It is noted that all synthetic steps involving Na/K alloy should be carried out with extreme caution under strict exclusion of air or moisture, under inert gas and appropriate personal protection (hood, blast shields, face shield, protective and fire resistant clothing) should be used and worn at all times. 1-Iodohexadecane, 1-iodooctane and 1-iodobutane were all obtained from Sigma-Aldrich and used as received without further purification. In-house deionized water was used during purification of the products.

Synthesis of Functionalized GNR Stacks and Intercalation Replacement

To an oven-dried 250 mL round-bottom flask containing a magnetic stir bar were added the MWNTs (100 mg, 8.3 mmol). The vessel was then transferred to a $N_2$ glove box where freshly distilled 1,2-dimethoxyethane (35 mL) and liquid Na/K alloy (0.29 mL) were added. The flask containing the suspension was then sealed with a septum and transferred out of the glove box where the suspension was dispersed by a short 5 min ultrasonication (using ultrasonic cleaner Cole-Parmer model 08849-00) to yield a dark greenish to red suspension. After ultrasonication, the reaction mixture was vigorously stirred (450 RPM) at room temperature for 3 d. The reaction suspension was then quenched by the addition of the 1-iodoalkane (8.75 mmol) using a syringe and left to stir at the room temperature for an additional day. Methanol (20 mL, 500 mmol) was then added to quench any excess Na/K alloy. The mixture was then stirred at room temperature for 10 min. For workup, the reaction mixture was filtered over a 0.45 μm pore size PTFE membrane. The filter cake was successively washed with THF (100 mL), i-PrOH (100 mL), $H_2O$ (100 mL), i-PrOH (100 mL), THF (100 mL), $Et_2O$ (10 mL) then Soxhlet extraction with THF was used for 3 d and the product dried in vacuum (~$10^{-2}$ mbar) for 24 h.

Electron Microscopy

Samples were dispersed in chlorobenzene and bath sonicated using an ultrasonic cleaner for 15 min for a quick dispersion. A drop was cast on a 100 nm $SiO_2$/Si substrate and large area low resolution images were taken at 20 kV under FEI Quanta 400 ESEM FEG scanning electron microscope and under a JEOL-6500 field-emission microscope.

Conductivity Measurements

Fabrication of HD-GNR devices was performed by tracking individual GNRs on the surface of 500 nm-thick thermal $SiO_2$ layer covered highly doped Si substrates by SEM (JEOL-6500 microscope), and followed by patterning of 20 nm-thick Pt contacts by standard electron beam lithography. The electrical transport properties were tested using a probe station (Desert Cryogenics TT-probe 6 system) under vacuum with chamber base pressure below $10^{-5}$ Torr. The IV data were collected by an Agilent 4155C semiconductor parameter analyzer.

Evolved Gas Analysis (EGA)

Thermogravimetric measurements were performed on a Netzsch 449 F3 Jupiter® instrument under a dynamic Ar (5.0) flow with a flow rate of 60 mL/min in a temperature range from 25° C. to 900° C. A heating rate of 10 K/min was used. About 5 mg of sample was placed in alumina ($Al_2O_3$) crucible. Simultaneously mass spectrometry was performed on MS 403C Aëolos® with detector SEM Chemeltron and system pressure of $2\times10^{-5}$ mbar. Gasses evolved under TG heat treatment were transferred to mass spectrometer through transfer capillary: quartz ID 75 μm which was heated up to 220° C. The upper limit of the mass spectrometer detector was 100 AMU.

XRD

X-ray powder diffraction (XRD) was performed using a Rigaku D/Max 2550 diffractometer with Cu Kα radiation ($\lambda$=1.5418 Å). Where necessary the data obtained was analyzed and processed using the Jade 9 software package.

GC-MS GC-MS was performed on Agilent Technologies 6890N Network GC system coupled to Agilent 5973 network mass selective detector.

SS $^{13}$C NMR spectroscopy

Spectra were obtained at 50.3 MHz $^{13}$C on a Bruker Avance 200 spectrometer with a probe for magic angle spinning (MAS) of rotors 4 mm in diameter. Chemical shifts are relative to the carbonyl carbon in glycine defined as 176.46 ppm. Both samples in FIG. 17 were dispersed in silica (10 wt % sample, 90 wt % silica). Parameters for the $^1H$—$^{13}C$ CP spectrum of functionalized and intercalated HD-GNRs (red curve in FIG. 17): 7.6 kHz MAS (so that any spinning sidebands are at multiples of + or −151 ppm from a centerband), 90° $^1H$ pulse=2.4 μs, contact time=1 ms with ramped amplitude proton pulse, FID=32.8 ms with spinal 64 decoupling, relaxation delay=5 s, number of scans=40,400, line broadening=50 Hz (1 ppm) used in processing the FID. Parameters for the $^1H$—$^{13}C$ CP/dipolar dephasing spectrum of functionalized and intercalated HD-GNRs (black curve in FIG. 17): as above except that a pair of 25-μs dephasing periods with a central 8.3-μs, 180° $^{13}C$ refocusing pulse immediately preceded FID acquisition. Parameters for the $^1H$—$^{13}C$ CP spectrum of functionalized and intercalated HD-GNRs heated at 900° C. for 20 min (blue curve in FIG.

17) are the same as for the unheated sample (red curve) except for 85,000 scans. Parameters for the $^1H—^{13}C$ CP spectrum of 100% silica (control sample) are the same except for 55,000 scans; no signal was detected.

Raman Spectroscopy

The Raman spectra were acquired using a Renishow Raman RE01 microscope with 40× lens; 514 nm wavelength laser was used for excitation.

Synthesis of Non-functionalized GNRs (H-GNRs)

To an oven-dried 250 mL round-bottom flask containing a magnetic stir bar were added the MWNTs (100 mg, 8.3 mmol). The vessel was then transferred to a $N_2$ glove box where freshly distilled 1,2-dimethoxyethane (35 mL) and liquid Na/K alloy (0.29 mL) were added. The flask with the suspension was then sealed with septa and transferred out of the glove box where it was dispersed by a short 5 min ultrasonication to yield a dark greenish to red suspension. After ultrasonication, the reaction mixture was vigorously stirred (450 RPM) at room temperature for 3 days. The reaction suspension was then quenched by the addition of methanol (20 mL, 500 mmol) using a syringe and stirring was continued at room temperature for 10 min. The reaction mixture was filtered over a 0.45 μm pore size PTFE membrane. The filter cake was successively washed with THF (100 mL), i-PrOH (100 mL), $H_2O$ (100 mL), i-PrOH (20 mL), THF (20 mL), $Et_2O$ (10 mL) and dried under in high vacuo.

Control Reaction of 1-iodohexadecane with Na/K in the Absence of MWNTs

The oven-dried 5 mL RB flask containing a magnetic stir bar were transferred to a $N_2$ glove box where freshly distilled 1,2-dimethoxyethane (DME, 40 mL) and liquid Na/K alloy (0.057 mL, 1.29 mmol) were added. The flask containing the suspension was then sealed with septa and transferred out of the glove box where the suspension was dispersed by a 5 min ultrasonication to yield a blue suspension. After ultrasonication, the reaction mixture was vigorously stirred (450 RPM) at room temperature for 1 h. The reaction suspension was then quenched by the addition of the 1-iodohexadecane (1 mL, 2.56 mmol) and left to stir at the room temperature for an additional day. The reaction mixture was then diluted with $CH_2Cl_2$ and GC-MS analysis was performed.

Control Reaction with Hexadecane and MWNTs

To an oven-dried 100 mL round-bottom flask and a magnetic stir bar were added MWNTs (100 mg; 8.33 mmol). The vessel was then transferred to a $N_2$ glove box where freshly distilled 1,2-dimethoxyethane (26 mL) and liquid Na/K alloy (0.13 mL; 3 mmol) were added. The flask containing the suspension was then sealed with septa and transferred out of the glove box where the suspension was dispersed by a short 5 min ultrasonication to yield a dark greenish to red suspension. After ultrasonication, the reaction mixture was vigorously stirred (450 RPM) at room temperature for 3 days. To the reaction suspension, hexadecane (0.6 mL; 3.34 mmol) was then added using a syringe and let to stir at the room temperature for an additional day. Reaction mixture was then quenched by addition of MeOH (21 mL) and allowed to stir at room temperature for 10 min. For workup, the reaction mixture was filtered over a PTFE membrane with a 0.45 μm pore size. The remaining solid was successively washed with THF (100 mL), i-PrOH (100 mL), $H_2O$ (100 mL), i-PrOH (20 mL), THF (20 mL), $Et_2O$ (10 mL) and dried under a high vacuo.

EXAMPLE 5

One-Pot Synthesis of Polymer-Functionalized Graphene Nanoribbons

In this Example, the preparation of polymer-functionalized graphene nanoribbons (PF-GNRs) in a "one-pot" synthesis is described. MWNTs were intercalated by potassium under vapor- or liquid-phase conditions, followed by addition of vinyl monomer, resulting in PF-GNRs. Scanning electron microscopy, thermogravimetric mass spectrometry and X-ray photoelectron spectroscopy were used to characterize the PF-GNRs. Also explored here is the correlation between the splitting of MWNTs, the intrinsic properties of the intercalants, and the degree of graphitization of the starting MWNTs.

Results and Discussion

Figure 21:
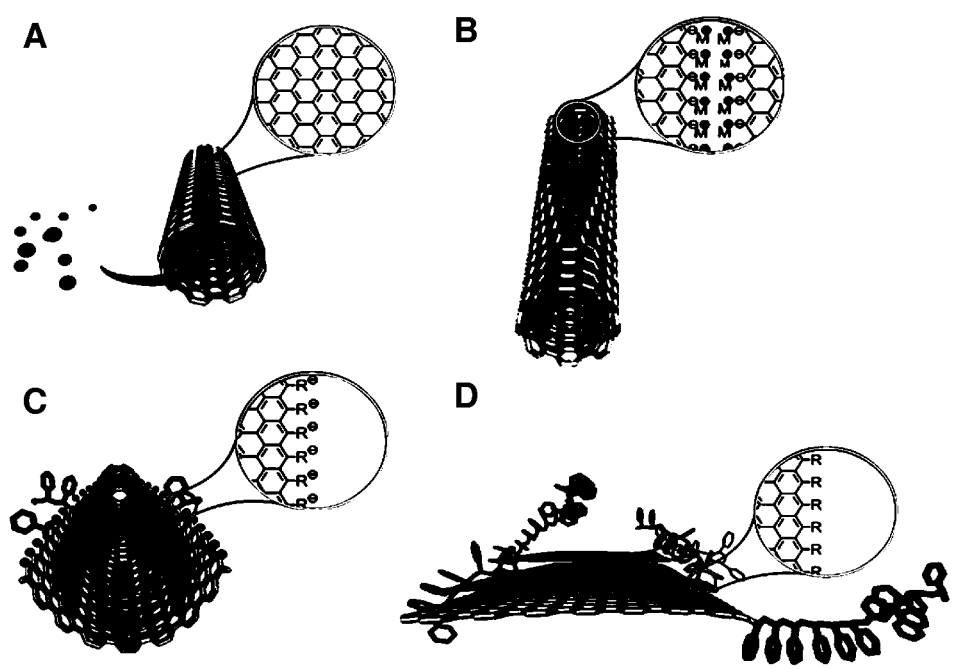
FIG. 21 provides a reaction scheme for the one-pot synthesis of polymer-functionalized GNRs (PF-GNRs).
Figure 22:
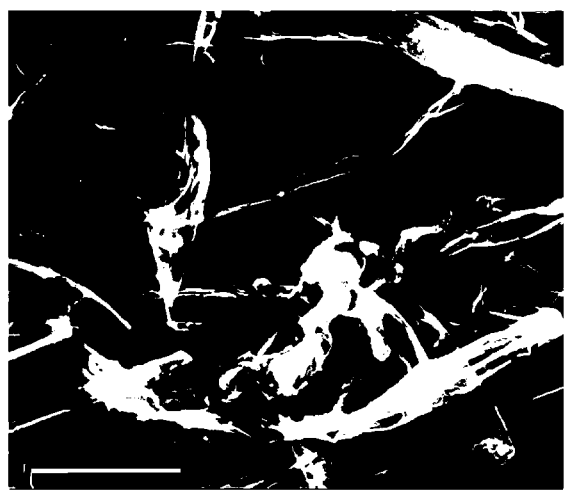
FIG. 22 provides a representative SEM image of MWNTs treated with potassium naphthalenide followed by addition of styrene. PF-GNRs can be readily identified under SEM. Their width is in the range of several hundred nm. The amorphous material on top of the GNRs is polystyrene.
Figure 23:
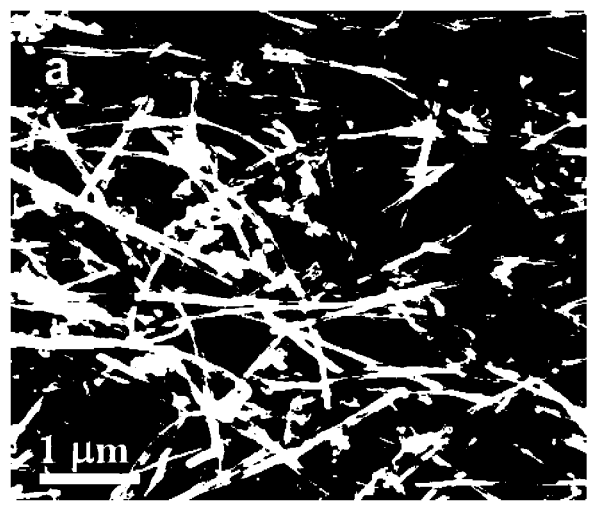
FIG. 23 shows SEM image of Mitsui MWNTs. Low-magnification (FIG. 23A) and high-magnification (FIG. 23B) SEM images are shown. The spherical nanoparticles are amorphous carbon byproducts. Thermal annealing at 2800° C. under argon atmosphere improved the structural integrity of MWNTs and removed polyaromatic hydrocabons and iron nanoparticles. The mean diameter of the MWNTs is 81±5 nm. The mean length is 8.19±1.7 μm.
Figure 23:
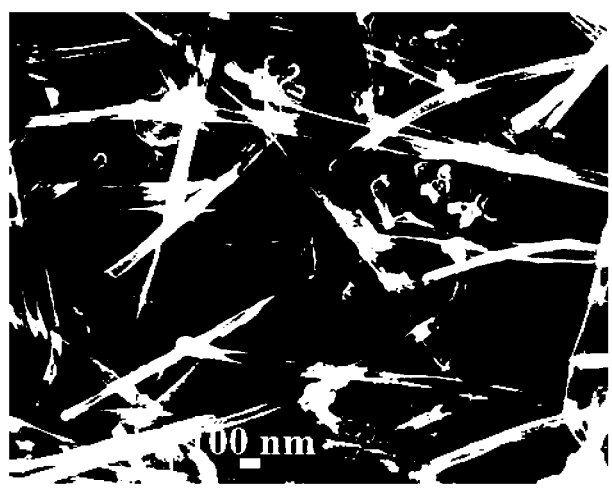
Figure 24:
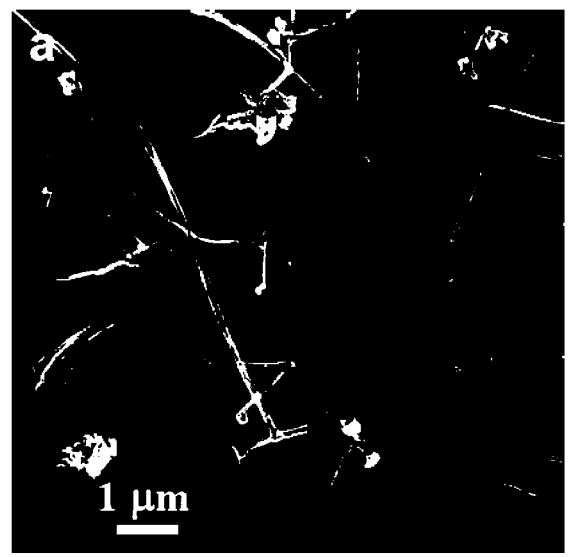
FIG. 24 shows additional images of PF-GNRs.
Figure 24:
Figure 25:
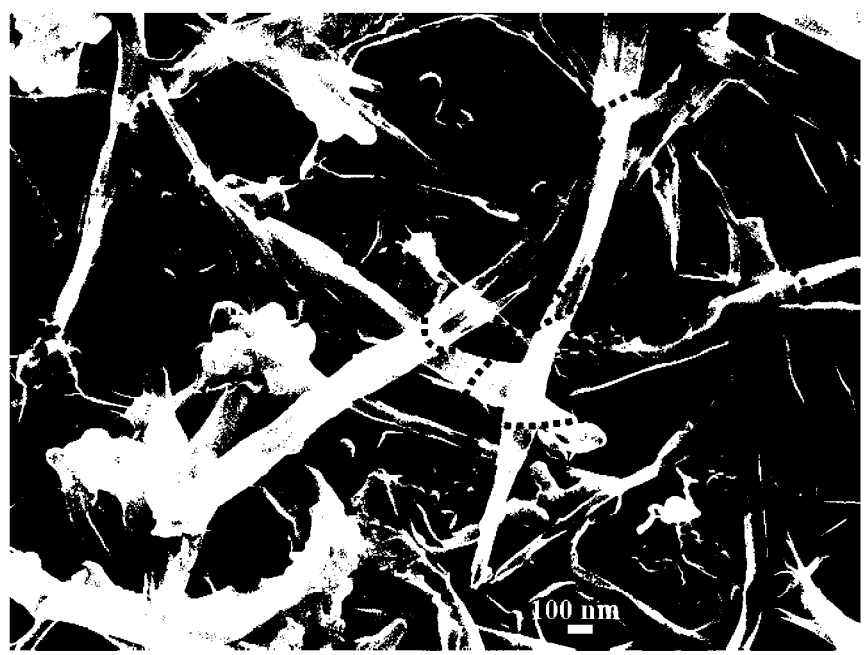
FIG. 25 is an SEM image of Mitsui MWNTs treated with potassium naphthalenide followed by addition of isoprene. The ribbon-like structures likely represent PF-GNRs (highlighted with dotted line). Thinner exfoliated MWNTs are also observed (highlighted with solid line). Since the sample was imaged before extraction with chloroform, amorphous polymer domains and spherical amorphous carbons can be observed.

The synthetic strategy for the one-pot synthesis of PF-GNRs used in the present study is shown in FIG. 21. MWNTs were converted into negatively charged polymerization macroinitiators via intercalation and splitting. Without being bound by theory, it is envisioned that the edges of the split tubes are lined by aryl anions and their associated metal cations. Second, anionic polymerization of unsaturated hydrocarbons between the negatively charged GNR edges and vinyl monomers results in PF-GNRs.

To produce PF-GNRs, MWNTs, potassium metal, naphthalene and tetrahydrofuran (THF) were charged into a Schlenk flask and then subjected to three freeze-thaw-pump cycles to remove oxygen. Without being bound by theory, it is envisioned that the intercalation of solvent-stabilized potassium cations into MWNTs may lead to expansion of the d-space between MWNT layers, thereby causing the MWNTs to partially split. The fissures on the sidewalls of the MWNTs can serve as the starting points for further splitting and exfoliation, as olefins, such as styrene and isoprene in the present case, are introduced. Only a small portion of olefin was enough to cause the splitting and exfoliation of MWNTs due to polymerization inside the nanotubes. However, excess olefin was used to consume the potassium naphthalenide.

Scanning electron microscopy (SEM) was used to image the MWNTs after intercalation and polymerization. PF-GNRs with widths in the range of several hundred nm are clearly shown in FIGS. 22-25.

Figure 26:
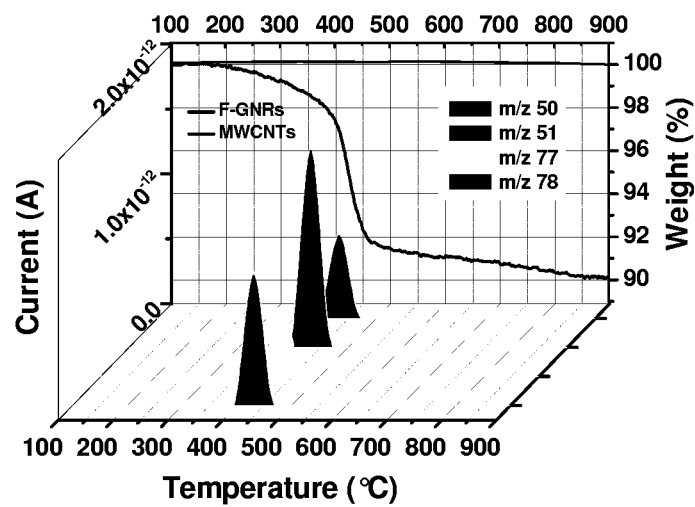
FIG. 26 provides data relating of PF-GNRs.
Figure 26:
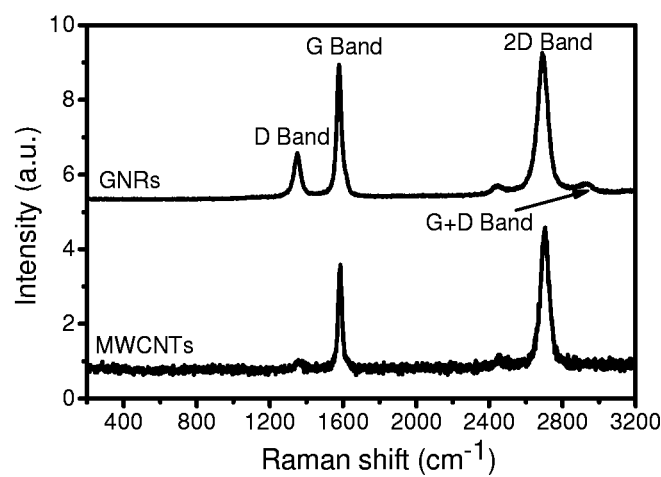
Figure 26:
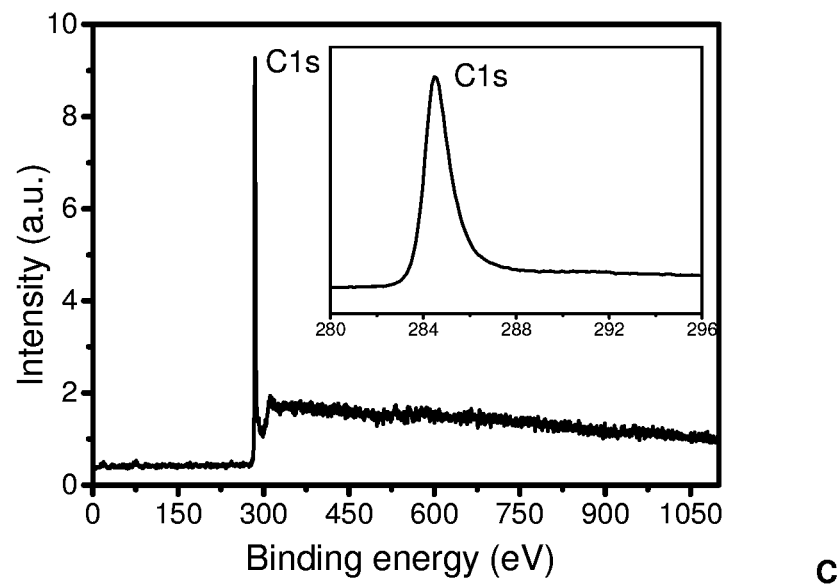

Thermogravimetric mass spectrometry (TG/MS) was used to qualitatively confirm the presence of the polystyrene chains, to estimate the quantity of the monomer units, and to determine temperature interval of degradation of PF-GNRs. See FIG. 26. To exclude the influence of the surface physisorbed components, all of the PF-GNRs were extracted by chloroform in a Soxhlet extractor for one week and then dried at 60° C. overnight. The thermogravimetric analysis (TGA) thermogram (FIG. 26A) indicates a one step process with a total weight loss of 9% between 100 and 900° C. Major decomposition occurred between 384° and 474° C. According to MS analysis and previous findings, this is the range where depolymerization of the polystyrene occurs.

Figure 27:
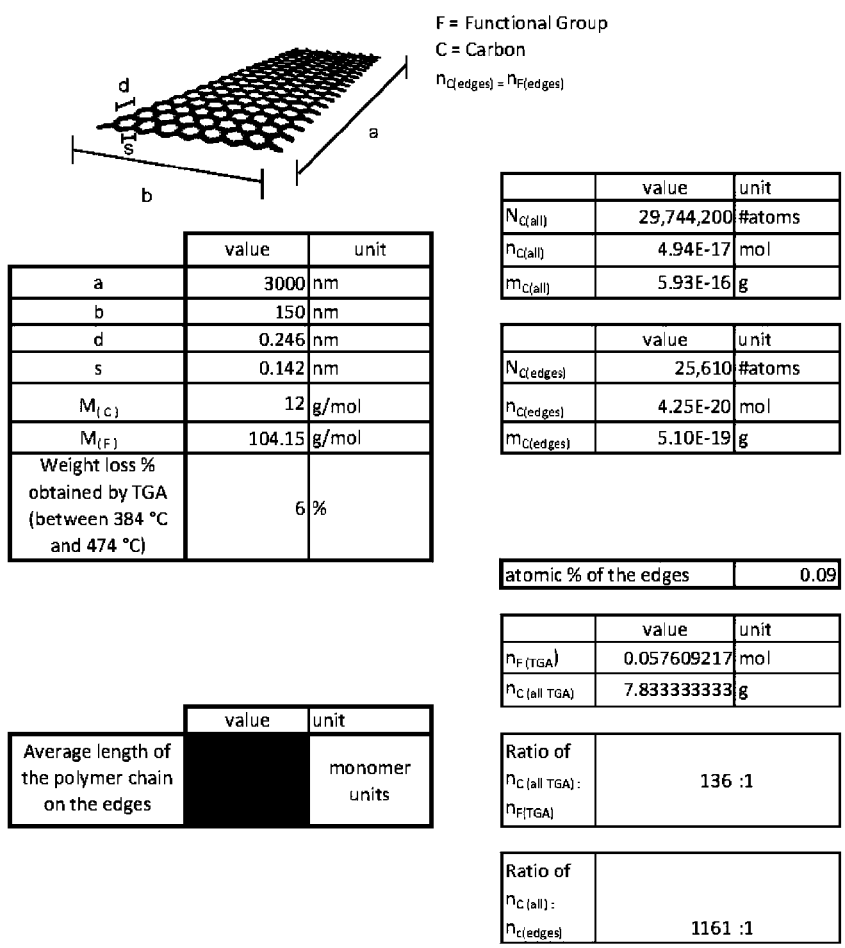
FIG. 27 provides a calculation of carbon atoms that functionalized with polymers in PF-GNRs.

Charged molecule fragments with mass to charge ratios (m/z) of 78, 77, 51, and 50 were also observed. Intensities that were distinct for the styrene monomer (an expected degradation product) were also observed. A control experiment with starting material MWNTs was also performed where no weight loss was observed (olive curve in FIG. 26A). Based on the weight loss between 384 and 474° C., the ratio between the styrene monomer unit and carbon atoms of the graphene material was 1:135. If all of the edge carbons of the graphene nanoribbons were functionalized, these data would mean that the average polymer chain length was 9 units for the 3 μm×150 nm ribbons. See FIG. 27.

Raman spectroscopy was also used to characterize the graphitic structure of the GNRs. An increase in the intensity of the D band over the G band from 0.15 for MWNTs to 0.35 for GNRs was observed. See FIG. 26B. Upon splitting of MWNTs, a prominent D peak is an indication of disorder in the graphene structure. The disordered structure also results in a slight broadening of the G band and the 2D band, as well as the combination mode of D+G band at ~2700 cm$^{-1}$ in GNRs. However, splitting of the G band, which corresponds to intercalated graphitic structure, was not observed in the Raman spectrum, implying that no residual intercalants or solvent were trapped in the GNRs. X-ray photoelectron spectroscopy (XPS) was used to examine the GNRs surface functionalities. The survey spectrum in FIG. 26C shows that no oxygen was detected in the GNRs. This is further confirmed by the high-resolution XPS C1s spectrum in the inset of FIG. 26C, as no peaks corresponding to 286 eV (C—O) or 287 eV (C=O) were observed.

Figure 28:
FIG. 28 provides data relating to various characteristics of potassium vapor treated MWNTs quenched with styrene.
Figure 28:
Figure 28:
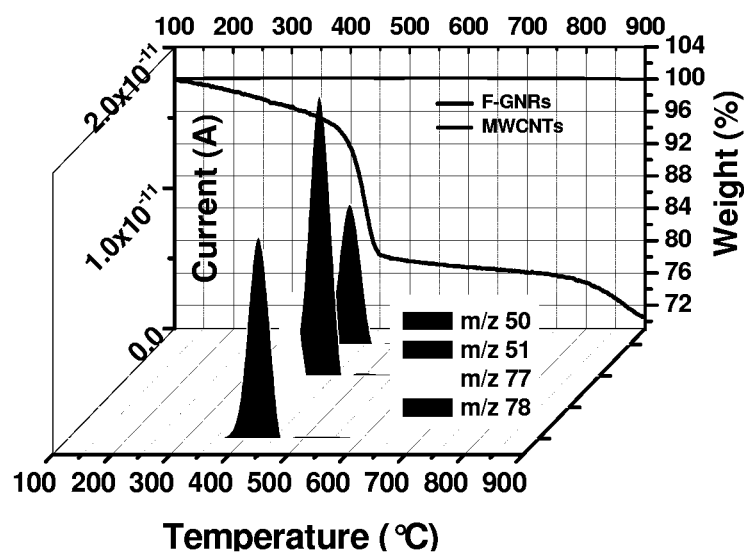

To further explore polymerization initiated by reactive GNR anions, MWNTs were potassium vapor-treated at 350° C. for 24 h. The product was transferred to a round-bottom flask in the glove box and styrene was added drop wise. The reaction mixture was kept at room temperature for 24 h and then at 60° C. overnight to complete the polymerization. The potassium intercalated MWNTs were fluffy and randomly distributed inside the flask. Addition of styrene monomer led to plastic beads with black centers, indicating the growth of polystyrene on MWNTs, as shown in FIG. 28A.

Figure 29:
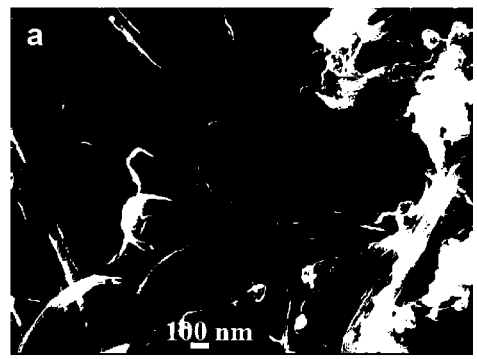
FIG. 29 provides additional SEM images of MWNTs and PF-GNRs.
Figure 29:
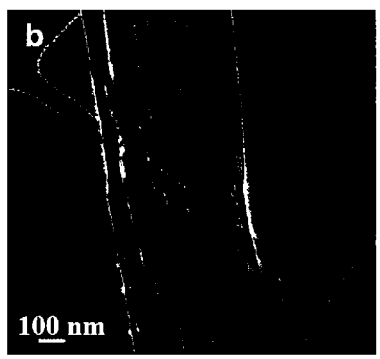
Figure 29:
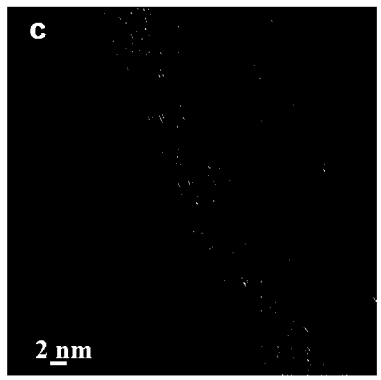

After the MWNTs were split, some ribbon-like structures were identified. See FIG. 28B. Additional images are shown in FIG. 29. Compared to liquid-phase intercalation followed by addition of monomer, quenching potassium vapor-treated MWNTs did not lead to further exfoliation of split MWNTs. The TGA in FIG. 28C shows that the weight loss was 22%, 4 times higher than that of MWNTs treated in liquid-phase intercalation. Furthermore, it is envisioned that the heat released from the anionic polymerization could initiate the polymerization of styrene, reducing the amount of monomer consumed by intercalated MWNTs. Therefore, liquid-phase intercalation of MWNTs followed by addition of monomer produces more functionalized GNRs than quenching potassium vapor treated MWNTs with monomer.

Figure 30:
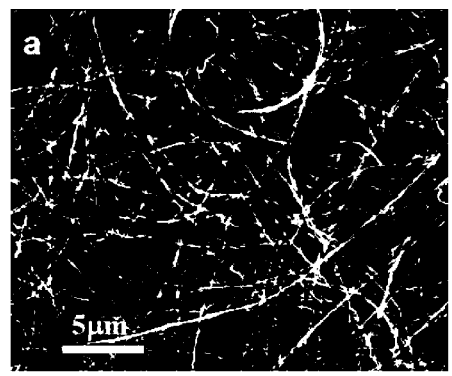
FIG. 30 provides SEM images of NTL MWNTs.
Figure 30:
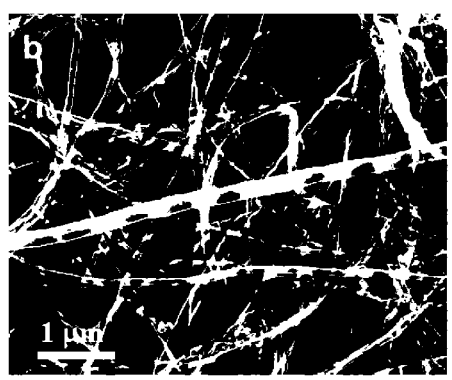
Figure 30:
Figure 31:
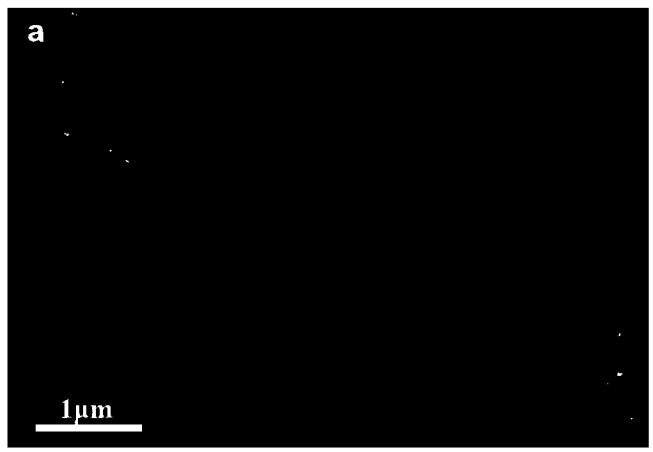
FIG. 31 shows SEM images of Baytubes.
Figure 31:
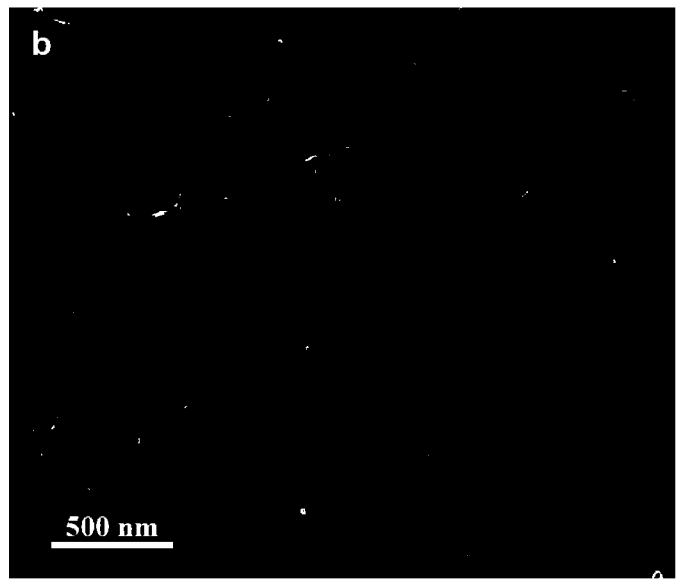

To explore the flexibility of the present protocol, two other MWNTs, NanoTechLabs MWNTs (NTL MWNTs) and Bayer MWNTs (Baytubes), were also subjected to the reaction conditions to compare the results to those from the Mitsui MWNTs. Upon liquid-phase intercalation followed by polymerization, NTL MWNTs were split but not further flattened to form GNRs. See FIG. 30. Most of the Baytubes MWNTs remained intact, although some partially flattened GNRs could be identified. See FIG. 31.

Without being bound by theory, it is envisioned that the charge transfer from naphthalene radical anions to the graphitic structure is governed by the electronic state of the host material. If the host materials are highly crystalline, overlap of the valence and conduction bands will lead to two carriers, electrons and holes in the conjugated graphene plane. Therefore, the electrons, during intercalation, can be transferred from the potassium naphthalenides to the host to balance the concentration of holes, and then into the graphene conduction band. Consequently, well-defined graphite intercalation compounds (GICs) can be obtained from highly crystallized hosts. For materials with a low degree of crystallinity, unorganized intercalation structures are observed, since there is no overlap between the conduction band and the valence band due to the disrupted graphitic structures.

Previous work on exfoliation of GICs suggests that forming a well-defined intercalation structure is the prerequisite for making exfoliated GNRs via polymerization-assisted exfoliation of MWNTs. The important link between the structural characteristics of the MWNTs host and splitting and exfoliation of MWNTs has been less explored, despite the fact that Mordkovich et al. studied the scroll carbon nanotubes via intercalating potassium metal into carbon nanotubes. *Carbon,* 1996, 34, 1301-1303.

The degree of graphitization can be calculated from the interplanar d spacing between two graphitic layers, according to Equation 3:

$$g=(0.3440-d_{002})/(0.3440-0.3354) \quad (Eq. 3)$$

Figure 32:
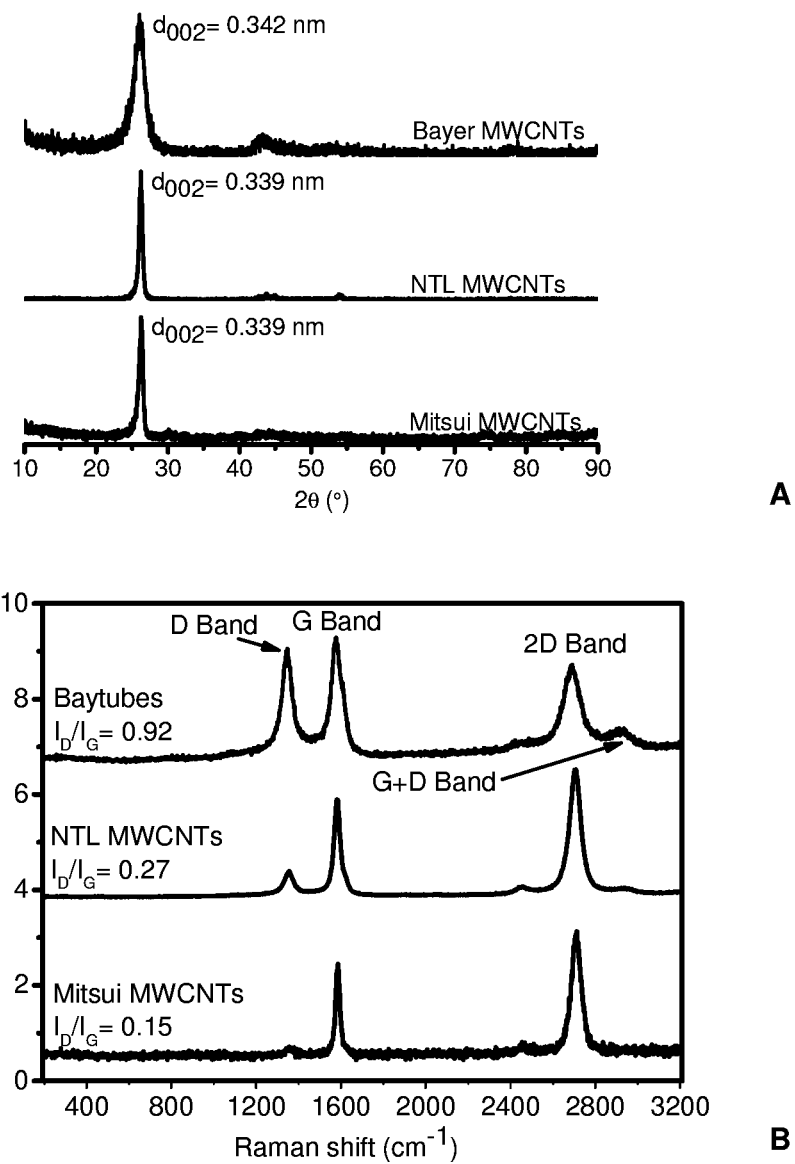
FIG. 32 provides spectral fingerprints of three different MWNTs.

In Equation 3, g is the degree of graphitization, 0.3440 (nm) is the interlayer spacing of the fully non-graphitized carbon, 0.3354 (nm) is the d spacing of the ideal graphite crystallite, and $d_{002}$ (nm), which is derived from X-ray diffraction (XRD) data, is the interlayer spacing corresponding to (002) planes of the graphitic material. The g for Mitsui MWNTs and NTL MWNTs is 0.58, which is higher than that for Bayer MWNTs (g=0.23). See FIG. 32A. Such results indicate easier exfoliation of the carbon host with higher graphitization.

The presence of any disordered structures caused by sp$^3$ carbon or defects that may terminate the splitting or exfoliation of MWNTs may not be determinable from XRD patterns. Consequently, Raman spectroscopy was used to differentiate the degree of disordered structure in the host materials by calculating the ratio of the intensity of the D band to the G band. The relative intensity of disorder-induced D band to crystalline G band, $I_D/I_G$, is 0.15 for Mitsui MWNTs, 0.27 for NTL MWNTs, and 0.92 for Baytubes. See FIG. 32B.

The defect sites on the graphene plane did not favor the formation of well-defined intercalation structures. Thus, the complete exfoliation of highly defective Baytubes by intercalation is more difficult. This is corroborated by recent work on reductive alkylation of MWNTs with potassium naphthalenide, in which the outer surface of highly defective MWNTs ($I_D/I_G$>1) were functionalized with decanoic acid. No ribbon-like structures were observed in the SEM images. Although NTL MWNTs are less defective, the flattening of ultra-long split tubes may require further treatment. Thus, most NTL MWNTs remained split and stacked rather than completely flattened. The precise establishment of the structural threshold (i.e. the critical value for g or $I_D/I_G$) that can be used to predict if the MWNTs can be split and exfoliated may be challenging. However, it is envisioned that higher degrees of graphitization of the carbon host (or the less defective degrees of the carbon host) might lead to more facile exfoliation of the MWNTs via intercalation.

Like the degree of graphitization of the starting carbon nanotubes, the ionization potential and the atomic size of the alkali metals also play an active role in intercalation and subsequent exfoliation. Since sodium naphthalenide and lithium naphthalenide have been used to make GICs and they are also commonly used as initiators for anionic polymerization, the intercalation of solvent-stabilized sodium and lithium into MWNTs for making functionalized GNRs was explored. Presumably, sodium naphthalenide (or lithium naphthalenide) can also turn MWNTs into macroinitiators and thus initiate the polymerization of unsaturated hydrocarbons. To verify this, MWNTs, sodium (or lithium) and naphthalene were dispersed in THF. Subsequently, the mixture was subjected to three freeze-thaw-pump cycles to remove oxygen. This was followed by addition of styrene.

Figure 33:
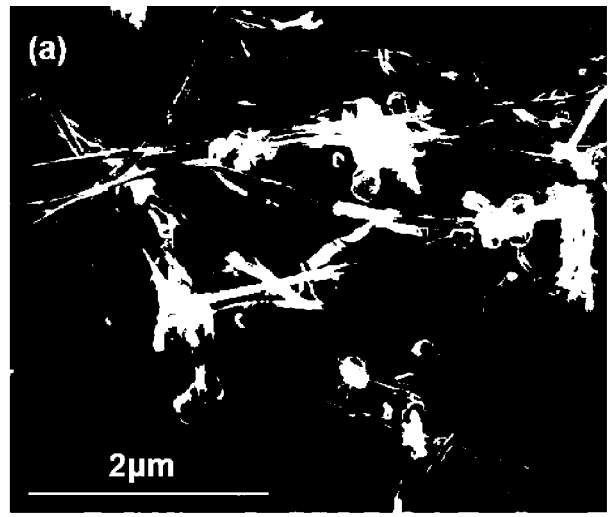
FIG. 33 provides representative SEM images of styrene treated alkali-metal intercalated MWNTs.
Figure 33:
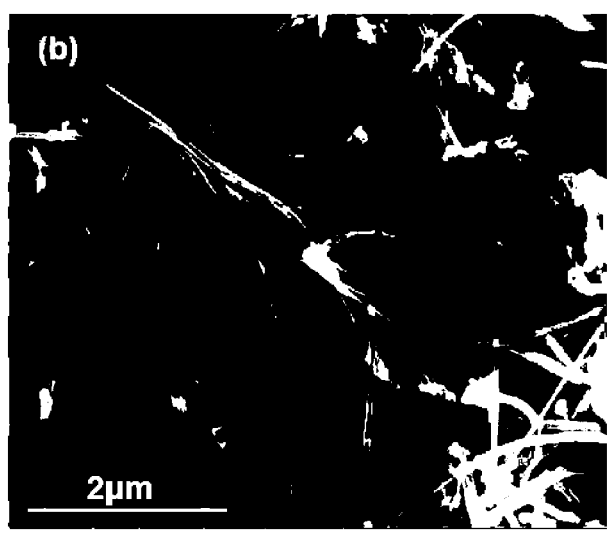

SEM images of the reaction products are shown in FIG. 33. Neither of the reaction products contained significant numbers of exfoliated MWNTs. In fact, most of the MWNTs remained intact, as shown by the SEM images in FIG. 33.

CONCLUSIONS

The wet chemical preparation of high-quality functionalized GNRs was achieved by polymerization-assisted exfoliation of MWNTs in a one-pot synthesis. The in situ functionalized GNRs were examined by TG/MS, SEM, TEM and Raman spectroscopy. Compared to MWNTs treated with potassium vapor followed by addition of isoprene, liquid-phase intercalation of MWNTs and subsequent polymerization was more efficient in exfoliating MWNTs to form functionalized GNRs, with less polymer bound onto the edges. Also demonstrated was the correlation between the structural characteristics of the host (the degree of graphitization and the intensity of D band over G band) and the exfoliation efficiency. The functionalized GNRs or split tubes could be used for reinforcing polymers. Functionalization of GNRs with electroactive polymers may contribute to further progress in nanoelectronics on the basis of favorable interactions that might be produced.

Materials and Methods

MWNTs were provided by Mitsui &Co. (lot no. 05072001K$_{28}$), NanoTechLabs, Inc. (lot no. #5T10M10), and Bayer Materials Science (lot no. C720P). The MWNTs were used as received. THF was treated with potassium hydroxide for several days, degassed and freshly distilled over sodium foils under nitrogen atmosphere. Styrene was passed through neutral alumina column and then degassed before use. Isoprene was distilled under nitrogen atmosphere. All chemicals were purchased from Sigma-Aldrich unless specified.

TG-MS measurements were performed using a Netzsch449 F3 Jupiter instrument under a dynamic Ar (99.999%) flow with a flow rate of 60 mL/min in a temperature range from 25° C. to 900° C. A heating rate of 10° C./min was used. About 5 mg of the sample was placed in an alumina ($Al_2O_3$) crucible. Simultaneous MS used a MS 403C Aëolos® with detector secondary electron multiplier Chemeltron and system pressure of $2 \times 10^{-5}$ mbar. Gasses evolved under TG heat treatment were transferred to MS detector using a quartz transfer capillary with an inside diameter of 75 µm that was heated to 220° C. The upper limit of the MS detector was 100 AMU. Raman spectroscopy was done using a Renishaw Raman RE01 microscopy with a 514.5 nm laser. The PF-GNRs were dispersed in ortho-dichlorobenzene using mild bath sonication (Cole-Parmer, EW-08849-00). The suspension was drop cast onto Si chips with 500 nm-thick $SiO_2$ layer. The solvent was evaporated upon heating. Next, the sample was imaged using a JEOL 6500 field-emission microscope and 2100F field emission gun transmission electron microscope.

To prepare PF-GNRs, 0.1 g of alkali metal (Li, Na, or K), 0.256 g of naphthalene and 50 mg of MWNTs (Mitsui MWNTs, NTL MWNTs or Baytubes) were added to a 100 mL oven dried Schlenk flask. 50 mL of THF was added. The flask was capped with a septum. Next, the suspension was subjected to three freeze-pump-thaw cycles to remove oxygen. The reaction mixture was stirred at room temperature for 3 days. 20 mL of monomer (styrene or isoprene) was added drop wise while cooling in a dry ice/acetone bath. The mixture was stirred at room temperature for 1 additional day. Next, the reaction mixture was quenched by 20 mL of anhydrous ethanol. The gray precipitate was filtered through a polytetrafluoroethylene (PTFE) membrane (0.45 µm), followed by extraction by boiling chloroform in a Soxhlet extractor for one week to remove unbound polymer. The final product (55 mg of PF-GNRs) was collected on a PTFE membrane (0.45 µm) and washed with THF (3×100 mL), ethanol (3×100 mL), DI water (3×100 mL), acetone (50 mL), and ether (50 mL). The washed product was then dried in a vacuum oven at 60° C. overnight.

Synthesis of PF-GNRs Through Vapor-Phase Intercalation

Details of making potassium intercalated MWNTs can be found in Example 4. The sealed reaction vessel loaded with potassium intercalated MWNTs was opened in a glove box. The intercalated tubes were transferred into a 50-ml round-bottom flask, followed by drop wise addition of 20 mL styrene monomer. The reaction mixture was taken out from the glove box and kept at room temperature for 24 hours and then at 60° C. overnight for completing the polymerization. The polystyrene/PF-GNRs mixture was dissolved in chloroform and precipitated by ethanol. After filtration, grey plastic chunks were cut into small pieces and extracted by chloroform with a Soxhlet extractor for one week. Finally, the black solid was collected on a PTFE membrane (0.45 µm). The product was washed with THF (3×100 mL), ethanol (3×100 mL), DI water (3×100 mL), acetone (50 mL), and ether (50 mL). Next, the product was dried in a vacuum oven at 60° C. overnight.

Alternatively, PF-GNRs can be prepared in a one-pot synthesis. This can involve heating the MWNTs and potassium chunks in a tightly capped Schlenk flask at 350° C. for 24 hours, followed by drop wise addition of styrene or isoprene through the stopcock under nitrogen at room temperature.

EXAMPLE 6

Unzipping of MWNTs by K/Na Alloys and Dry Ice

In this Example, Applicants opened MWNTs by K/Na alloys in the presence of dimethyl ether (DME). Thereafter, the opened MWNTs were functionalized with $CO_2$ to form carboxyl-functionalized GNRs (GNR—(COOH)$_n$). The reaction is illustrated in the following scheme:

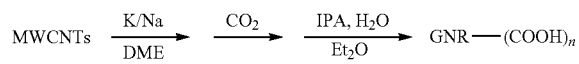

In particular, Applicants used K/Na alloy (0.9 mL) to intercalate MWNTs (600 mg, also referred to as MWCNTs) in dimethoxyethane (DME, 120 mL). The reaction was then quenched with dry ice (around 0.5 kg), which is the solid form of $CO_2$. Finally, the product was washed with isopropanol (IPA, 100 mL), $H_2O$ (100 mL), and ethyl ether ($Et_2O$, 100 mL). The MWNTs used were Mitsui MWNTs. The derived product was GNR—(COOH)$_n$.

Figure 34:
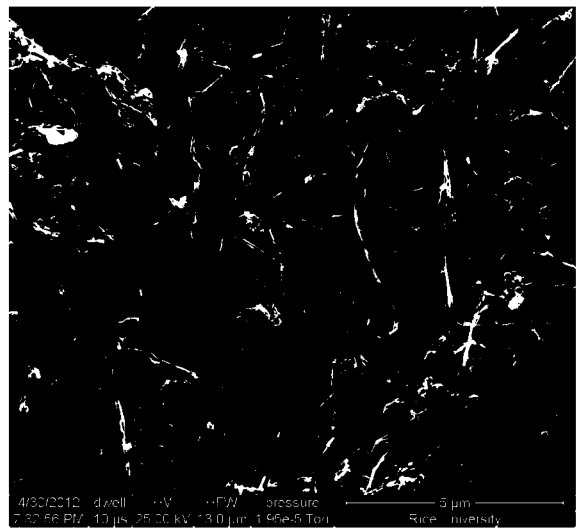
FIG. 34 provides SEM images of carboxyl-functionalized GNRs (GNR—(COOH)n). The scale bar in FIG. 34A is 5 μm. The scale bar in FIG. 34B is 2 μm.
Figure 34:
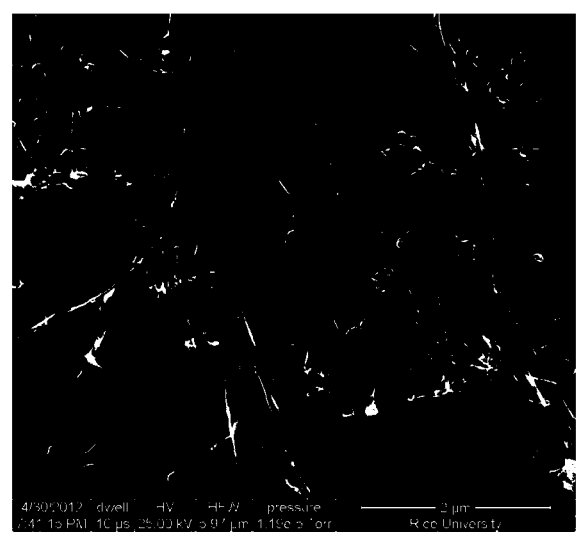
Figure 35:
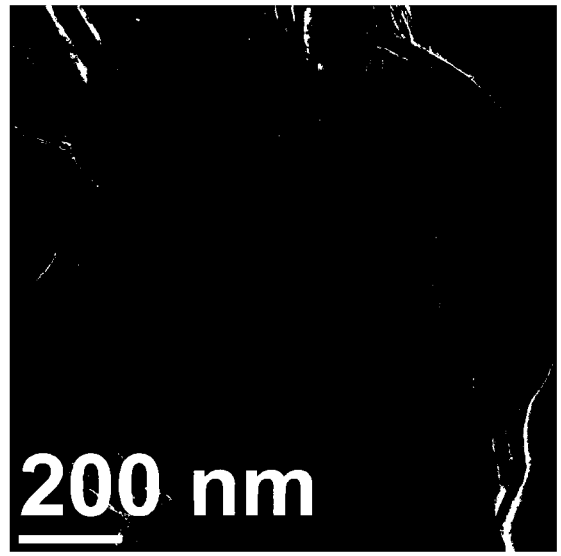
FIG. 35 provides TEM images of GNR—(COOH)n. The scale bar in FIG. 35A is 200 nm. The scale bar in FIG. 35B is 10 nm.
Figure 35:
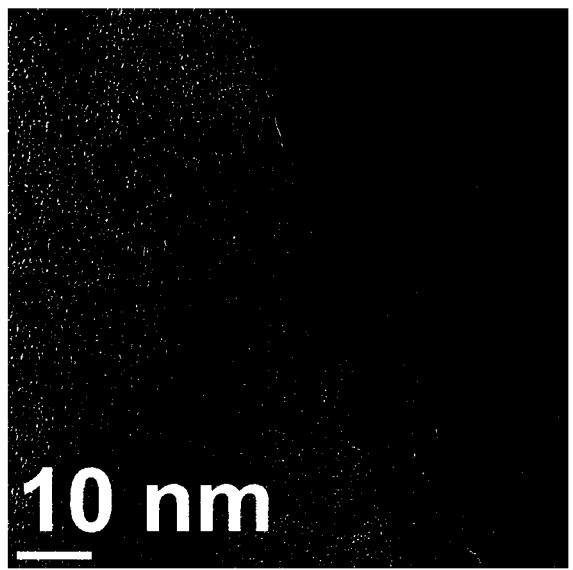
Figure 36:
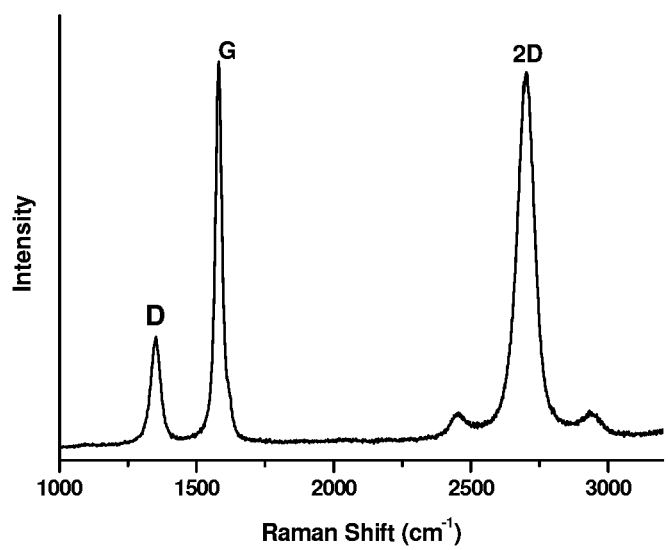
FIG. 36 provides the Raman spectrum of GNR—(COOH) n. The excitation laser wavelength is 514 nm.

The products were characterized by SEM (FIG. 34), TEM (FIG. 35), and Raman (FIG. 36). SEM images showed that the products are mostly ribbon structures, indicating a high unzipping efficiency. See FIGS. 34A-B.

In preparing the TEM samples, Applicants dispersed the products in $H_2O$ by adding a surfactant and sonicating the solution for 10 minutes in a probe sonicator. The TEM images showed that the GNR—(COOH)$_n$ products are fully unzipped with 3-5 layers. See, e.g., FIGS. 35A-B.

The Raman spectrum showed that there is a D peak. See FIG. 36. In addition, the Raman spectrum showed that the ratio of D peak to G peak is 1:3. The Raman spectrum utilized a 514 nm excitation laser.

Without being bound by theory, Applicants envision that the dry ice played an important role in unzipping and exfoliating the MWNTs. At room temperature, dry ice can sublimate readily, thereby producing an ample amount of $CO_2$ gas. When K intercalated MWNTs were quenched with dry ice, K reacted with $CO_2$, thereby leading to the functionalization of MWNTs. At the same time, the generated gas formed in this process aided in the exfoliation of the GNRs to fewer layers.

This is the first time that Applicants have demonstrated the gas-mediated exfoliation of GNRs. Thus, it is envisioned that the use of $CO_2$ or other volatile components or gases can be used to assist in the exfoliation of GNR stacks into fewer layers of graphene nanoribbons, or even an individual layer of graphene nanoribbon.

Without further elaboration, it is believed that one skilled in the art can, using the description herein, utilize the present disclosure to its fullest extent. The embodiments described herein are to be construed as illustrative and not as constraining the remainder of the disclosure in any way whatsoever. While the embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A method of preparing graphene nanoribbons, wherein the method comprises:
   exposing a plurality of carbon nanotubes to an alkali metal source in the presence of an aprotic solvent, wherein the exposing opens the carbon nanotubes parallel to their longitudinal axis; and
   exposing the opened carbon nanotubes to a protic solvent to form unfunctionalized graphene nanoribbons.

2. The method of claim 1, wherein the method takes place at room temperature.

3. The method of claim 1, wherein the carbon nanotubes are selected from the group consisting of single-walled carbon nanotubes, double-walled carbon nanotubes, triple-walled carbon nanotubes, multi-walled carbon nanotubes, ultra-short carbon nanotubes, and combinations thereof.

4. The method of claim 1, wherein the alkali metal source is selected from the group consisting of lithium, potassium, sodium, rubidium, cesium, alloys thereof, and combinations thereof.

5. The method of claim 1, wherein the aprotic solvent is selected from the group consisting of diethyl ether, tetrahydrofuran, 1,4-dioxane, glyme, 1,2-dimethoxyethane, diglyme, tetraglyme, amines, N,N,N',N'-tetramethylethylenediamine, triethylamine, 1,4-diazabicyclo[2.2.2]octane, trialkylamines, dialkylarylamines, alkyldiarylamines, dimethylformamide, and combinations thereof.

6. The method of claim 1, wherein the protic solvent is selected from the group consisting of formic acid, n-butanol, isopropanol, n-propanol, ethanol, methanol, acetic acid, water, hydrochloric acid, sulfuric acid, ammonia, diethyl amine, dialkylamines, monoalkylamines, diarylamines, monoarylamines, monoalkymonoarylamines, and combinations thereof.

7. The method of claim 1, further comprising a step of adding an electrophile to the unfunctionalized graphene nanoribbons, wherein the electrophile functionalizes the graphene nanoribbons.

8. The method of claim 7, wherein the electrophile is selected from the group consisting of water, alcohols, organic halides, alkenes, alkynes, alkyl halides, acyl halides, allylic halides, benzyl halides, benzylic halide, alkenyl halides, aryl halides, alkynyl halides, fluoralkly halides, perfluoroalkyl halides, aldehydes, ketones, methyl vinyl ketones, esters, sulfonate esters, acids, acid chlorides, carboxylic acids, carboxylic esters, carboxylic acid chlorides, carboxylic acid anhydrides, carbonyl bearing compounds, enones, nitriles, carbon dioxide, halogens, monomers, vinyl monomers, ring-opening monomers, isoprenes, butadienes, styrenes, acrylonitriles, methyl vinyl ketones, methacrylates, 1,4-dimethoxy-2-vinylbenzene, methyl methacrylate, alkyl acrylates, alkyl methacrylates, trimethylsilyl chlorides, tert-butyldimethylsilyl chlorides, triphenylsilyl chlorides, epoxides, carbon dioxide, carbon disulfide, tert-butanol, 2-methylpropene, bromine, chlorine, iodine, fluorine, and combinations thereof.

9. The method of claim 7, wherein the electrophile is carbon dioxide.

10. The method of claim 7, wherein the electrophile is a monomer.

11. The method of claim 10, wherein the monomer is selected from the group consisting of olefins, vinyl monomers, styrenes, isoprenes, butadienes, acrylonitriles, methyl vinyl ketones, alkyl acrylates, alkyl methacrylates, ring opening monomers, epoxides, and combinations thereof.

12. The method of claim 10, wherein the monomer polymerizes upon addition to the graphene nanoribbons, thereby forming polymer-functionalized graphene nanoribbons.

13. The method of claim 7, wherein the adding of electrophiles leads to the formation of edge-functionalized graphene nanoribbons.

14. The method of claim 1, wherein the formed graphene nanoribbons have a conductivity ranging from about 0.1 S/cm to about 9,000 S/cm.

15. The method of claim 7, further comprising a step of deintercalating functional groups from one or more layers of graphene nanoribbons.

16. The method of claim 15, wherein the deintercalating occurs by heating the formed graphene nanoribbons.

17. The method of claim 1, further comprising a step of exfoliating one or more layers of graphene from the formed graphene nanoribbons.

18. The method of claim 17, wherein the exfoliating comprises exposure of the graphene nanoribbons to a gas, wherein the gas is selected from the group consisting of carbon dioxide, nitrogen gas, hydrogen gas, hydrogen chloride, air, and combinations thereof.

* * * * *